United States Patent
Shinoda

(10) Patent No.: US 9,233,346 B2
(45) Date of Patent: Jan. 12, 2016

(54) DROPLET COLLISION SUBSTANCE MIXING APPARATUS AND DROPLET COLLISION SUBSTANCE MIXING METHOD

(75) Inventor: Masataka Shinoda, Tokyo (JP)

(73) Assignee: SONY CORPORATION, Tokyo (JP)

( * ) Notice: Subject to any disclaimer, the term of this patent is extended or adjusted under 35 U.S.C. 154(b) by 940 days.

(21) Appl. No.: 13/377,230

(22) PCT Filed: May 28, 2010

(86) PCT No.: PCT/JP2010/003594
§ 371 (c)(1),
(2), (4) Date: Dec. 9, 2011

(87) PCT Pub. No.: WO2010/146778
PCT Pub. Date: Dec. 23, 2010

(65) Prior Publication Data
US 2012/0080544 A1  Apr. 5, 2012

(30) Foreign Application Priority Data
Jun. 16, 2009 (JP) .................. 2009-143081

(51) Int. Cl.
| | | |
|---|---|---|
| *B01F 5/02* | (2006.01) | |
| *B01F 13/00* | (2006.01) | |
| *B01F 15/02* | (2006.01) | |
| *B01L 3/02* | (2006.01) | |
| *B01L 3/00* | (2006.01) | |

(52) U.S. Cl.
CPC ........... *B01F 5/0256* (2013.01); *B01F 13/0071* (2013.01); *B01F 15/0203* (2013.01); *B01F 15/0246* (2013.01); *B01L 3/0268* (2013.01); *B01L 3/502776* (2013.01); *B01L 3/502784* (2013.01); *B01L 2200/0673* (2013.01); *B01L 2400/027* (2013.01); *B01L 2400/0439* (2013.01)

(58) Field of Classification Search
CPC ...................................................... B01F 5/0256
USPC ............................................. 366/162.4, 127
See application file for complete search history.

(56) References Cited

U.S. PATENT DOCUMENTS

| | | | | |
|---|---|---|---|---|
| 3,380,584 | A * | 4/1968 | Fulwyler | ............................ 209/3 |
| 4,005,435 | A * | 1/1977 | Lundquist et al. | ............... 347/75 |
| 4,341,310 | A * | 7/1982 | Sangiovanni et al. | ......... 209/638 |
| 5,180,065 | A * | 1/1993 | Touge et al. | ................... 209/577 |

(Continued)

FOREIGN PATENT DOCUMENTS

| | | |
|---|---|---|
| JP | 11-262644 | 9/1999 |
| JP | 2001-124789 | 5/2001 |

(Continued)

*Primary Examiner* — Charles Cooley
*Assistant Examiner* — Marc C Howell
(74) *Attorney, Agent, or Firm* — Hazuki International, LLC

(57) ABSTRACT

A substance mixing apparatus that is capable of uniformly mixing a certain amount of trace substances and also mixing minute particles. A substance mixing apparatus includes two or more flow paths (11, 12, 13) in which orifices (111, 121, 131), from which a fluid that flows therethrough is externally discharged, are formed, oscillation devices (112, 122, 132) that form droplets of the fluid discharged from each of the orifices (111, 121, 131) by oscillating at least the orifice (111, 121, 131) part of the flow paths at a predetermined oscillation frequency and discharge the droplets, and a device for causing the droplets (A, B, C) discharged from the orifices (111, 121, 131) of the flow paths (11, 12, 13) to collide with one another.

16 Claims, 15 Drawing Sheets

(56) References Cited

U.S. PATENT DOCUMENTS

| | | |
|---|---|---|
| 6,200,013 B1 | 3/2001 | Takeuchi et al. |
| 6,478,414 B2 * | 11/2002 | Jeanmaire ..................... 347/77 |
| 6,719,211 B2 * | 4/2004 | Takeuchi et al. .......... 239/102.2 |
| 6,802,640 B2 * | 10/2004 | Schubert et al. .......... 366/181.6 |
| 2002/0096577 A1 | 7/2002 | Takeuchi et al. |
| 2005/0079644 A1 * | 4/2005 | Sakurada ..................... 438/26 |

FOREIGN PATENT DOCUMENTS

| | | |
|---|---|---|
| JP | 2002-139370 | 5/2002 |
| JP | 2005-296883 | 10/2005 |

* cited by examiner (A)

(B)

DROPLET COLLISION SUBSTANCE MIXING APPARATUS AND DROPLET COLLISION SUBSTANCE MIXING METHOD

CROSS REFERENCE TO RELATED APPLICATIONS

The present application is a national stage of International Application No. PCT/JP2010/003594 filed on May 28, 2010 and claims priority to Japanese Patent Application No. 2009-143081 filed on Jun. 16, 2009, the disclosures of which are incorporated herein by reference.

BACKGROUND

The present invention relates to a substance mixing apparatus and a substance mixing method, more specifically, to an apparatus and method for mixing substances by causing droplets discharged from orifices of two or more flow paths to collide with one another.

In recent years, in fields of biotechnology and chemistry, an increase in scale and speed of a reaction analysis process is progressing. For realizing a high throughput of the reaction analysis process, it is effective to simultaneously analyze a large number of micro reaction systems. With a large amount of reaction systems, when carrying out an analysis on a substance having an extremely high reaction speed, for example, a reaction progresses in a part of the reaction systems before mixing of all the reaction systems is ended. As a result, a large number of reaction systems cannot be analyzed under the same condition, and an accurate analysis result cannot be obtained.

On the other hand, with micro reaction systems, there is a problem that it becomes difficult to uniformly mix substances in a certain amount. When the amounts of substances vary among the reaction systems or substances are mixed without uniformity, reproducibility of the analysis is lowered, and a reliable analysis result cannot be obtained.

As a technique that enables trace substances to be mixed uniformly in a certain amount, Patent Document 1 discloses a uniformly mixing method and a uniformly mixing device for a substance that are characterized by including two or more piezoelectric type fluid droplet discharge means, and in that small fluid droplets discharged from the fluid droplet discharge means are caused to collide with one another to be uniformly mixed. According to this technique, a mixing-reaction operation of a minute amount of substances becomes possible, and the substances can be caused to react uniformly so that a uniform reactant can be obtained. It should be noted that the "piezoelectric type fluid droplet discharge means" adopted in the uniformly mixing method for a substance and the like is a fluid droplet discharge apparatus that generates a pressure in a fluid compression chamber by deforming a partial wall portion of the fluid compression chamber by a piezoelectric/electrostrictive device to thus inject a fluid in the fluid compression chamber from a nozzle hole.

Patent Document 1: Japanese Patent Application Laid-open No. Hei 11-262644

DISCLOSURE OF THE INVENTION

Problems to be Solved by the Invention

Conventionally, in the fields of biotechnology and chemistry, biologically-relevant minute particles such as a cell, a microorganism, and a liposome, and synthetic minute particles such as latex particles, gel particles, and industrial particles have been mixed with various compounds, and a reaction of the minute particles and the compounds has been analyzed.

As an example, in the field of biotechnology, lymphocytes and antigens are mixed in a large number of wells to screen antigen-specific B cells coupled with the antigens, or lymphocytes are mixed with cancer cells or virus-infected cells in the wells to screen cellular disorder T cells that have caused a destruction of the cancer cells and the like. The detected antigen-specific B cells and cellular disorder T cells are subjected to a gene analysis after retrieval and used in developments of antibody drugs and cell immunity treatments. In the screenings, lymphocytes are dispensed singly or plurally to the wells to be mixed with antigens and the like, and a high throughput screening called "single-cell screening" for detecting a reaction and an object cell is carried out.

In the uniformly mixing method and mixing apparatus for a substance disclosed in Patent Document 1 above, although a certain amount of trace substances can be mixed uniformly, mixing of such minute particles with a substance and mixing of minute particles with minute particles are not assumed.

In this regard, the present invention mainly aims at providing a substance mixing apparatus that is capable of uniformly mixing trace substances in a certain amount and also mixing minute particles.

Means for Solving the Problems

For solving the problems above, according to the present invention, there is provided a substance mixing apparatus including: two or more flow paths in each of which an orifice, from which a fluid that flows therethrough is externally discharged, is formed; an oscillation device that forms droplets of the fluid discharged from each of the orifices by oscillating at least the orifice part of the flow paths at a predetermined oscillation frequency and discharges the droplets; and means for causing the droplets discharged from the orifices of the flow paths to collide with one another.

The substance mixing apparatus further includes: a detection means for detecting minute particles included in the fluid that flows through the flow paths; and a control means for calculating a flow sending interval of the minute particles based on a detection signal of the minute particles from the detection means and controlling the oscillation frequency of the oscillation device based on the calculated flow sending interval. The control means controls the oscillation frequency such that a predetermined number of minute particles are incorporated in the droplets discharged from the orifices of the flow paths through which the fluid including the minute particles flows.

Moreover, the substance mixing apparatus further includes: a charge means for imparting a charge to the droplets discharged from the orifices; and paired electrodes provided oppositely along a movement direction of the droplet obtained by the collision. The movement direction of the droplet obtained by the collision is controlled by an electric action force generated by the charge imparted to the droplets discharged from the orifices and the paired electrodes. By controlling the movement direction of the droplet obtained by the collision, the droplets can be retrieved in two or more areas.

Alternatively, the substance mixing apparatus may further include a drive means for relatively moving the orifices of the flow paths with respect to two or more areas for retrieving and accommodating the droplet obtained by the collision. By relatively moving the orifices of the flow paths with respect to the areas, the droplet obtained by the collision can be retrieved in the two or more areas.

In the substance mixing apparatus, it is favorable for the flow paths to be formed on a single microchip. The present invention also provides a microchip including two or more flow paths in each of which an orifice, from which a fluid that flows therethrough is externally discharged, is formed and that form droplets of the fluid discharged from each of the orifices by an oscillation of at least the orifice part and discharge the droplets, the flow paths being provided such that the droplets discharged from the orifices collide with one another.

In the microchip, a predetermined part of the flow paths is structured as a detection portion for detecting minute particles included in the fluid that flows through the flow paths, and a cross-sectional area of the orifice part of the flow paths is smaller than that of the detection portion.

In the microchip, a minute pipe that introduces a laminar flow of a second fluid including minute particles in a laminar flow of a first fluid that flows through the flow paths may be provided upstream from the detection portion in a fluid feeding direction.

It is favorable for the minute pipe to be formed of metal to which a voltage can be applied. Accordingly, the minute pipe can be structured as a charge means for imparting a charge to the droplets discharged from the orifices.

The microchip may further include an oscillation device that oscillates at least the orifice part of the flow paths.

Further, the present invention provides a substance mixing method including: arranging two or more flow paths in each of which an orifice, from which a fluid that flows therethrough is externally discharged, is formed; forming droplets of the fluid discharged from the orifices by oscillating at least the orifice part of the flow paths at a predetermined oscillation frequency and discharging the droplets; and causing the droplets discharged from the orifices of the flow paths to collide with one another.

In the substance mixing method, a fluid including minute particles may be caused to flow through either one of the flow paths, and the droplets that include the minute particles and are discharged from the orifice of the flow path may be caused to collide with the droplets discharged from the orifice of the other flow path, to thus mix the minute particles with a substance. In this case, by controlling the oscillation frequency based on a flow sending interval of the minute particles included in the fluid that flows through the flow paths, a predetermined number of minute particles can be incorporated in the droplets discharged from the orifices of the flow paths.

The substance mixing method may further include: imparting a charge to the droplets discharged from the orifices; controlling a movement direction of the droplet obtained by the collision by an electric action force generated by paired electrodes provided oppositely along the movement direction of the droplet obtained by the collision and the charge imparted to the droplets; and dispensing the droplet obtained by the collision to two or more areas. Alternatively, the droplet obtained by the collision may be dispensed to two or more areas by relatively moving the orifices of the flow paths with respect to the areas.

In the substance mixing method, it is favorable for the flow paths to be formed on a single microchip.

In the present invention, the "minute particles" widely include biologically-relevant minute particles such as a cell, a microorganism, and a liposome, and synthetic minute particles such as latex particles, gel particles, and industrial particles.

The biologically-relevant minute particles include chromosomes constituting various cells, liposomes, mitochondria, and organelle (cell organelle). Target cells include animal cells (hemocyte cells) and plant cells. The microorganisms include bacterium such as *Bacillus coli*, viruses such as a tobacco mosaic virus, and fungi such as a yeast. The biologically-relevant minute particles may also include biologically-relevant polymers such as a nucleic acid, a protein, and a complex of those. Moreover, the industrial particles may be, for example, an organic or inorganic polymer material or metal. The organic polymer material includes polystyrene, styrene-divinylbenzen, and polymethylmethacrylate. The inorganic polymer material includes glass, silica, and a magnetic material. The metal includes a gold colloid and aluminum. The shape of the minute particles is normally a sphere, but may instead be a nonspherical shape, and the size and mass are also not particularly limited.

SUMMARY

According to the present invention, a substance mixing apparatus that is capable of uniformly mixing trace substances in a certain amount and also mixing minute particles can be provided.

Additional features and advantages of the present invention are described in, and will be apparent from, the following Detailed Description and the FIGS.

DETAILED DESCRIPTION

Figure 1:
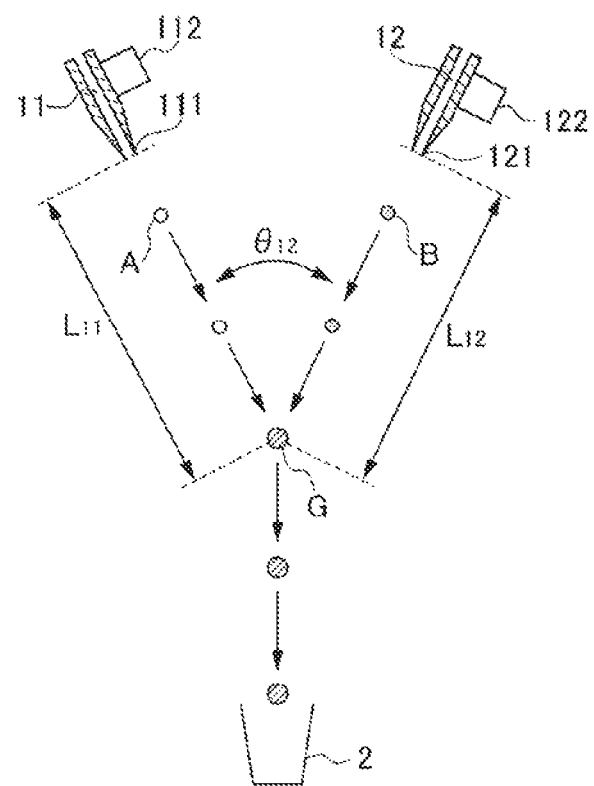
FIG. 1 A diagram for explaining a first embodiment of a substance mixing apparatus according to the present invention.

Hereinafter, favorable embodiments for embodying the present invention will be described with reference to the drawings. It should be noted that the embodiments described below are mere examples of representative embodiments of the present invention, and the range of the present invention should not be interpreted narrowly with this. It should be noted that descriptions will be given in the following order.
1. Collision Means
    (1-1) First Embodiment
    (1-2) Second Embodiment
2. Detection Means and Control Means
3. Dispense of Mixed Droplets
    (3-1) Dispense by Charge Means
    (3-2) Dispense by Drive Means
4. Microchip-type Substance Mixing Apparatus
    (4-1) General Overview of Apparatus Structure
    (4-2) Microchip
    (4-3) Dispense by Charge Means
    (4-4) Dispense by Drive Means
1. Collision Means
    (1-1) First Embodiment FIG. 1 is a schematic diagram for explaining a first embodiment of a substance mixing apparatus according to the present invention. The substance mixing apparatus of this embodiment has characteristics that substances are mixed by causing droplets discharged from orifices of two flow paths to collide with one another. The figure shows a structure of means equipped in the substance mixing apparatus for causing droplets to collide with one another.

In the figure, the reference numerals 11 and 12 denote flow paths through which fluids including substances to be mixed flow. In the flow paths 11 and 12, orifices 111 and 121 for externally discharging the flowing fluids are formed. Further, the reference numerals 112 and 122 denote oscillation devices that oscillate at least the orifice 111, 121 part of the flow paths 11 and 12 at a predetermined oscillation frequency to thus form droplets of the fluids to be discharged from the orifices 111 and 121 and discharge them. The oscillation devices 112 and 122 are each constituted of a piezo-oscillation device or the like and provided so as to apply a predetermined oscillation to the entire flow paths 11 and 12 or a part including at least the orifice 111, 121 part.

The fluids including the substances to be mixed are sent to the flow paths 11 and 12 by a fluid feeding means (not shown) and discharged as droplets A and B from the orifices 111 and 121 by the function of the oscillation devices 112 and 122. At this time, by adjusting a fluid feeding amount (flow rate) with respect to the flow paths 11 and 12, diameters of the orifices 111 and 121, an oscillation frequency of the oscillation devices 112 and 122, and the like, sizes of the droplets A and B can be adjusted, and substances can be incorporated into the droplets in a certain amount. The discharged droplets A and B become a single droplet G by colliding with each other at a predetermined position in a space outside the flow paths 11 and 12, and the substances included in the droplets A and B are mixed in the droplet G. The droplet G flies according to an inertia of the droplets A and B and retried in a vessel denoted by the reference numeral 2 in the figure. A collision angle $\theta_{12}$ of the droplets A and B and flying distances $L_{11}$ and $L_{12}$ to the collision position are set as appropriate based on a flying speed or size of the droplets A and B, a discharge interval from the orifices 111 and 121, and the like so as to enable the droplets A and B to collide with one another.

In the substance mixing apparatus, by discharging the fluids including the substances to be mixed from the orifices 111 and 112 of the flow paths 11 and 12 as the droplets A and B and causing them to collide with one another, the substances included in the droplets can be uniformly mixed in a short time. Moreover, since substances can be incorporated into the droplets A and B by a certain amount, variances in the amount of mixed substances are not caused.

The fluid that flows through the flow path 11 or 12 may include 1 or 2 or more substances so that the 1 or 2 or more substances included in the droplet A and the 1 or 2 or more substances included in the droplet B are mixed in the droplet G by the collision of the droplets A and B.

The collision angle $\theta_{12}$ of the droplets A and B and the distances $L_{11}$ and $L_{12}$ to the collision position can be set as appropriate based on the flying speed or size of the discharged droplets A and B, the discharge interval from the orifices 111 and 121, and the like.

Figure 2:
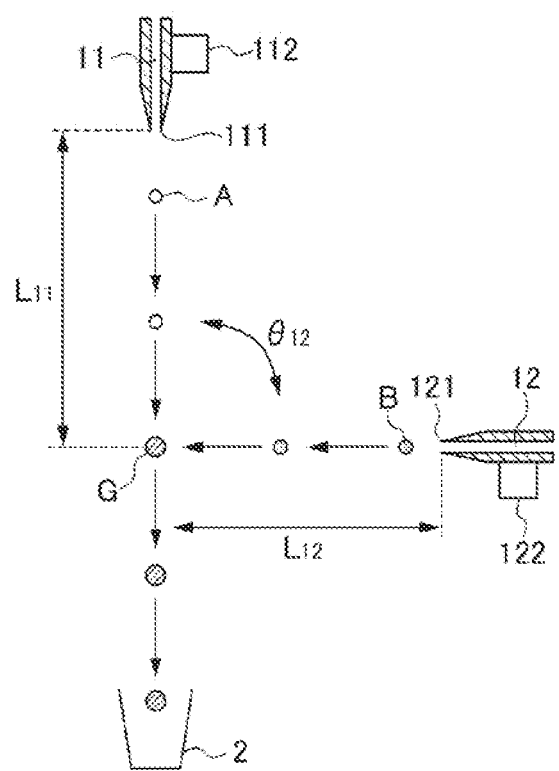
FIG. 2 A diagram for explaining a modified example of the first embodiment of the substance mixing apparatus according to the present invention.

For example, as shown in FIG. 2, it is possible to set the flow paths 11 and 12 at almost 90 degrees so that the collision angle $\theta_{12}$ of the droplets A and B discharged from the orifices of the flow paths becomes almost 90 degrees. The collision angle of the droplets can be set as appropriate to be larger than 0 degree and smaller than 180 degrees.

FIG. 2 shows a setting position of the vessel 2 in a case where, since the mass of the droplet B is sufficiently smaller than that of the droplet A, a flying direction of the droplet G after the collision does not vary as compared to the discharge direction of the droplet A. Since the droplet G flies according to the inertia of the droplets A and B, the vessel 2 needs to be placed in a direction in which the droplet G flies.

It should be noted that in the first embodiment shown in FIG. 1 and a modified example shown in FIG. 2, all of the droplets A and B do not need to collide to be mixed, and there may be a droplet A that does not collide with the droplet B. Moreover, there may be a droplet B that does not collide with the droplet A. For example, a droplet B discharged from the orifice 121 can be mixed with a droplet A discharged from the orifice 111 at a two-to-one ratio. In this case, the droplet A itself that did not collide with the droplet B and the droplet G obtained by colliding and mixing with the droplet B are retrieved in the vessel 2. The droplet B can be caused to collide with the droplet A at a two-to-one ratio by adjusting the flying distances $L_{11}$ and $L_{12}$ to the collision position of the droplets A and B, the discharge interval from the orifices, and the like.

(1-2) Second Embodiment

Figure 3:
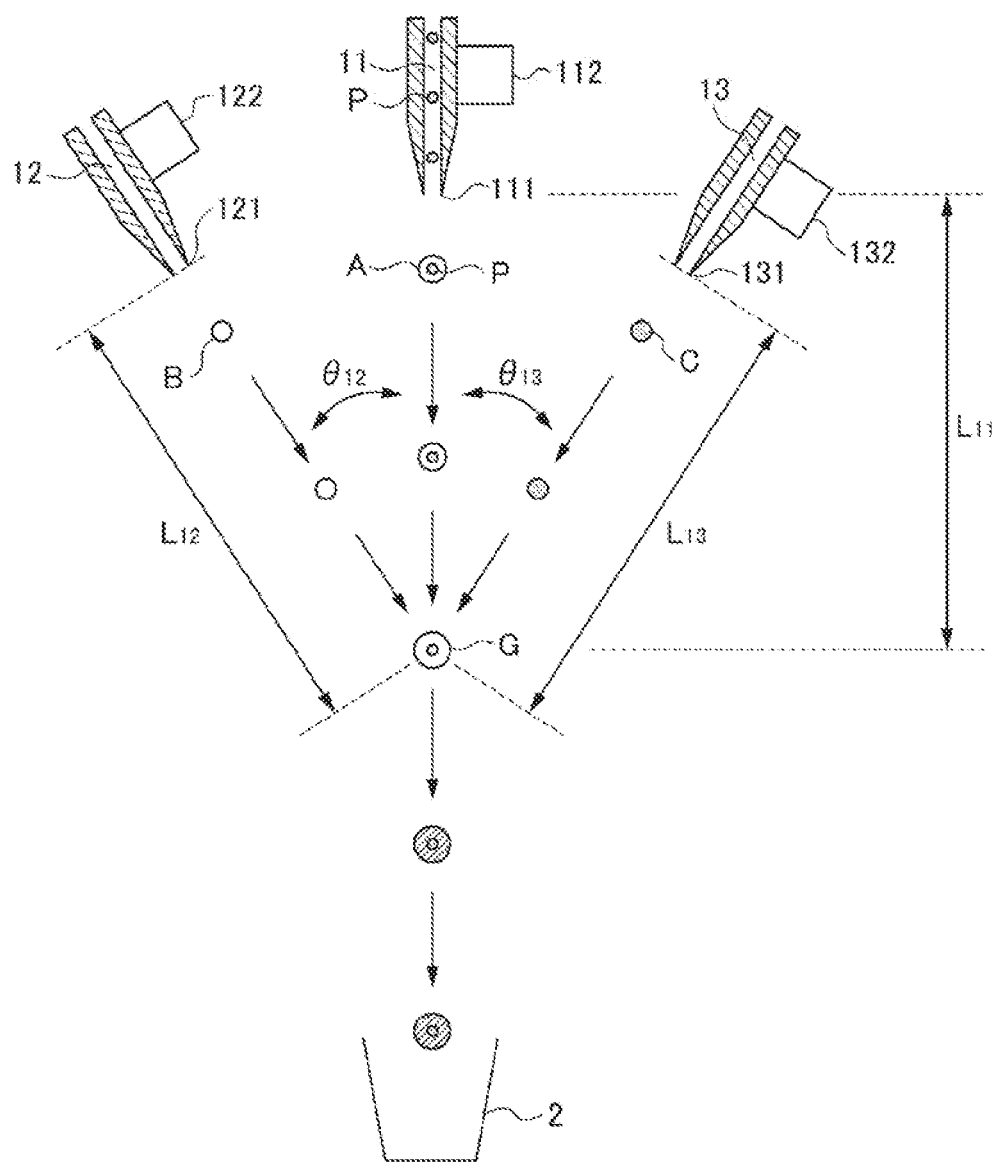
FIG. 3 A diagram for explaining a second embodiment of the substance mixing apparatus according to the present invention.

FIG. 3 is a schematic diagram for explaining a second embodiment of the substance mixing apparatus according to the present invention. The substance mixing apparatus of this embodiment has characteristics that a fluid including minute particles is discharged from an orifice of one flow path and caused to collide with droplets discharged from orifices of other two flow paths to thus mix the substances including minute particles. The figure shows a structure of means equipped in the substance mixing apparatus for causing the droplets to collide with one another.

In the figure, the reference numerals 11, 12, and 13 denote flow paths through which fluids including substances to be mixed flow. Of those, a fluid including minute particles P flows through the flow path 11. Orifices 111, 121, and 131 for externally discharging the flowing fluids are formed in the respective flow paths, and oscillation devices 112, 122, and 132 for forming droplets of the fluids to be discharged from the orifices and discharging them are provided.

The fluids including the substances to be mixed are sent to the flow paths by a fluid feeding means (not shown) and discharged as droplets A, B, and C from the orifices by the function of the oscillation devices. Of those, the droplets A discharged from the orifice 111 include the minute particles P included in the fluid that flows through the flow path 11. The discharged droplets A, B, and C become a single droplet G by colliding with one another at a predetermined position in a space outside the flow paths 11, 12, and 13, and the minute particles P included in the droplet A are mixed with substances included in the droplets B and C in the droplet G. After that, the droplet G flies according to an inertia of the droplets A, B, and C and retried in the vessel 2.

The collision angle $\theta_{12}$ of the droplets A and B, a collision angle $\theta_{13}$ of the droplets A and C, and the flying distances $L_{11}$, $L_{12}$, and $L_{13}$ to the collision positions of the droplets are set as appropriate based on a flying speed or size of the droplets, a discharge interval from the orifices, and the like so as to enable the droplets to collide with one another.

In the substance mixing apparatus, the fluid including the minute particles P is discharged from the orifice 111 of the flow path 11 as a droplet A, and the fluids including substances to be mixed are discharged from the orifices 121 and 132 of the flow paths 12 and 13 as droplets B and C. By causing those droplets to collide with one another, the minute particles and substances included in the droplets can be uniformly mixed within a short time. Moreover, since the substances can be incorporated into the droplets B and C by a certain amount, a plurality of substances can be mixed with the minute particles P without causing variances in the amounts.

Figure 4:
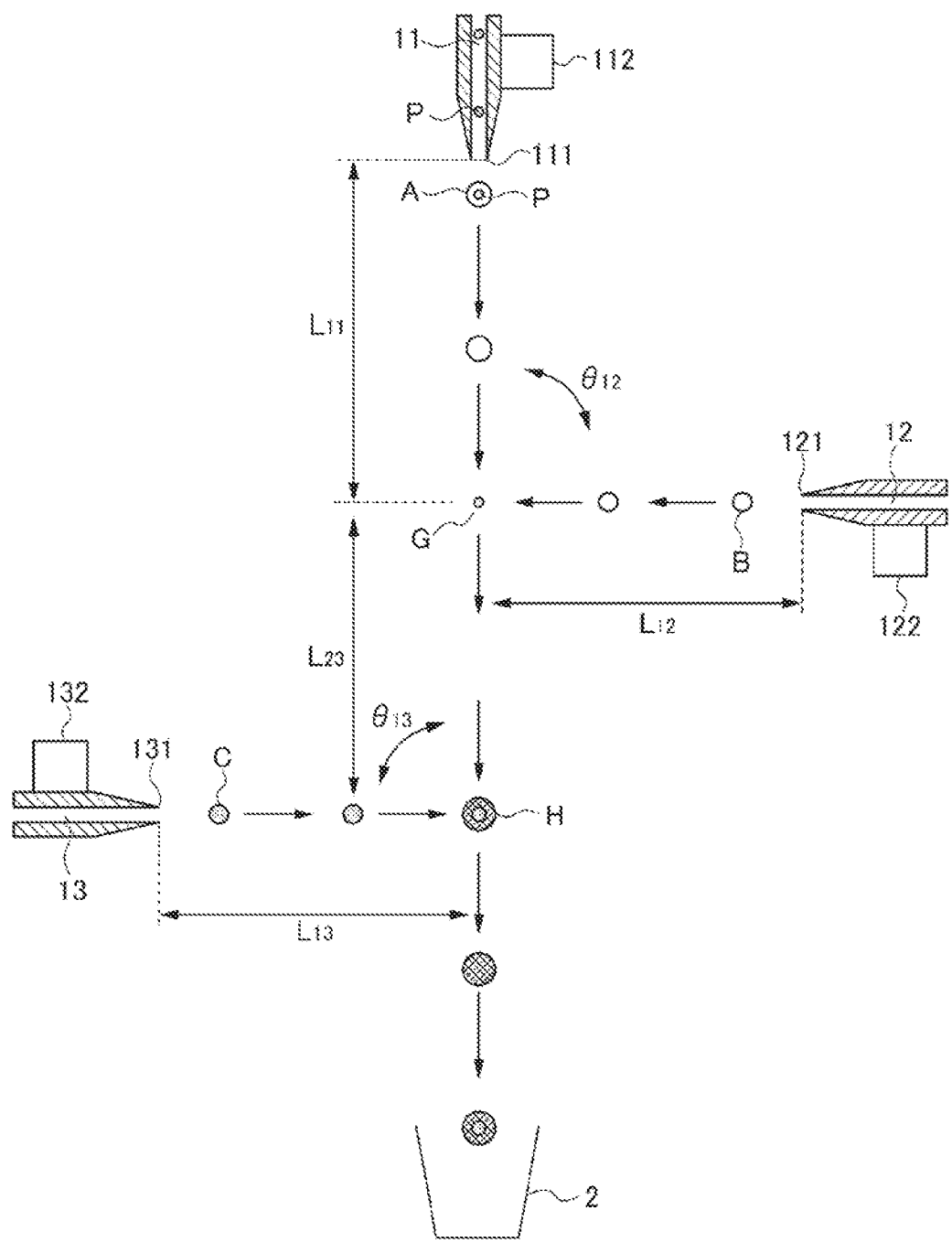
FIG. 4 A diagram for explaining a modified example of the second embodiment of the substance mixing apparatus according to the present invention.

In mixing the droplets A, B, and C, collision and mixing of the three droplets may be carried out at the same time, or collision and mixing of any of the two droplets may be carried out first. Collision and mixing of the droplets can be carried out at arbitrary timings. For example, as shown in FIG. 4, the flow paths 11 and 12 are set almost at 90 degrees so that the droplet A that is discharged from the orifice 111 and includes the minute particles P first collides with the droplet B discharged from the orifice 121 to thus obtain a droplet G. Accordingly, the minute particles P and substance included in the droplets A and B are mixed. Next, the flow path 13 is set almost at 90 degrees with respect to the flying direction of the droplet G so that the droplet C discharged from the orifice 131 collides with the droplet G to thus obtain a droplet H. Accordingly, the minute particles and substance included in the droplets H and C can be mixed.

Further, all of the droplets A, B, and C do not always need to collide and be mixed, and only two of those may collide to be mixed. The combination of the droplets to undergo collision and mixing can be set arbitrarily. For example, the droplet B discharged from the orifice 121 can be caused to collide with the droplet A discharged from the orifice 111 at a two-to-one ratio and be mixed therewith. In this case, the droplet that collides with the droplet C discharged from the orifice 131 is the droplet A itself or the droplet G in which the droplets A and B are mixed. Then, by selecting a combination of the droplets A and G and the droplet C discharged from the orifice 131 for collision, a mixture of the droplets A and C, a mixture of the droplets A, B, and C, or a mixture of the droplets A and B can be obtained as the droplet H to be eventually retrieved in the vessel 2. The combination of the droplets for collision and mixing can be set arbitrarily by adjusting the flying distances $L_{11}$, $L_{12}$, $L_{23}$, and $L_{13}$ to the collision positions of the droplets, the flying speeds of the droplets A, B, and C, the discharge interval from the orifices, and the like.

Although the cases where the substances are mixed by providing two flow paths 11 and 12 in FIGS. 1 and 2 and three flow paths 11, 12, and 13 in FIGS. 3 and 4 have been described, the number of flow paths to be provided is not particular limited in the substance mixing apparatus according to the present invention, and 4 or more flow paths may be provided.

2. Detection Means and Control Means

Figure 5:
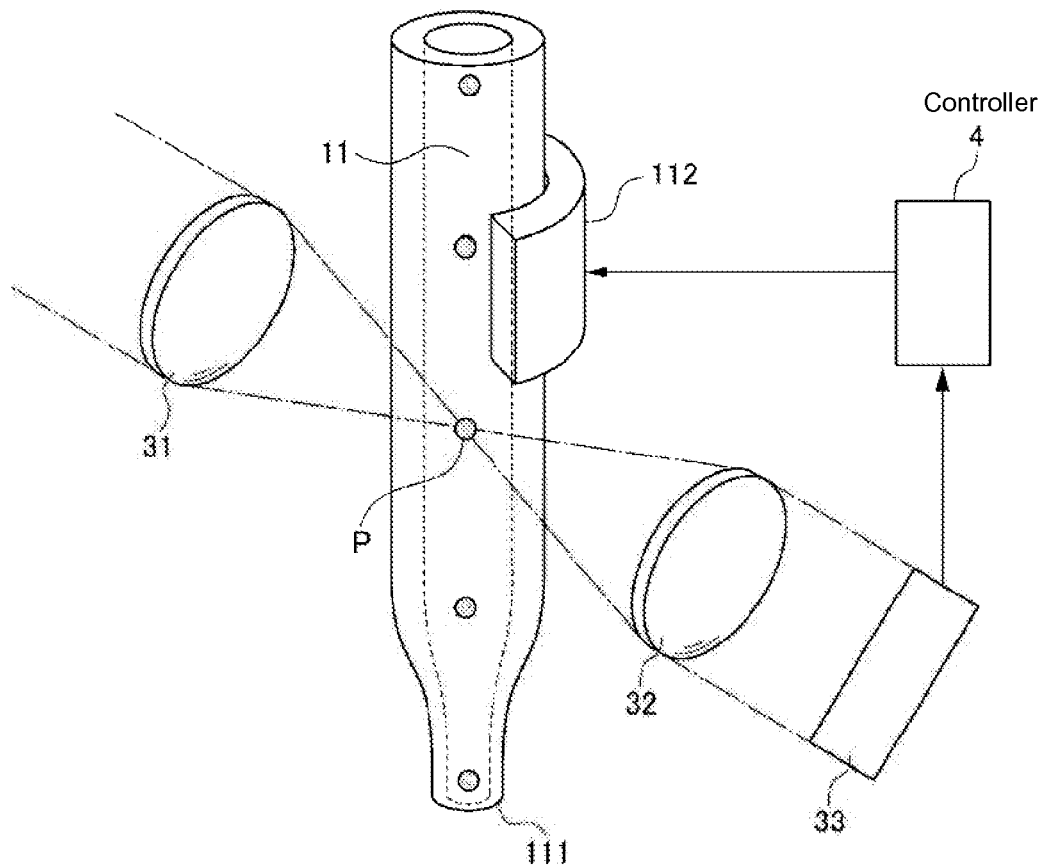
FIG. 5 A diagram for explaining a detection means and a control means equipped in the substance mixing apparatus according to the present invention.

FIG. 5 is a schematic diagram for explaining a structure for incorporating a predetermined number of minute particles in a droplet to be discharged from the orifice of the flow path in the substance mixing apparatus according to the present invention.

As described with reference to FIGS. 3 and 4, in the substance mixing apparatus according to the present invention, droplets including minute particles are discharged from the orifice of the flow path and caused to collide with the droplets discharged from the orifice of the other flow path to thus mix substances including the minute particles. At this time, the number of minute particles included in a droplet is not particularly limited and can be set arbitrarily. FIG. 3 has shown the example where one minute particle P is incorporated in the droplet A discharged from the orifice 111 of the flow path 11. Moreover, FIG. 4 has shown the example where 0 or 1 minute particle P is incorporated in every other droplet A discharged from the orifice 111 of the flow path 11.

The number of minute particles to be incorporated in a droplet can be set to an arbitrary number of 0 or 1 or more by adjusting the fluid feeding amount (flow rate) with respect to the flow paths, the diameter of the orifices, the oscillation frequency of the oscillation devices, and the like. The number of minute particles to be incorporated in a droplet can be favorably controlled by controlling the oscillation frequency of the oscillation devices in particular, the details of which will be given hereinafter with reference to FIG. 5.

In FIG. 5, the reference numerals 31, 32, and 33 each denote a detection means for detecting the minute particles P included in the fluid that flows through the flow path 11. The detection means 31, 32, and 33 irradiate laser light (measurement light) onto the flowing minute particles P at a predetermined part of the flow path 11 and convert detected light generated from the minute particles P (measurement target light) into electric signals.

The detection means 31, 32, and 33 can be constituted of a laser light source, an irradiation system 31 (detection means 31) constituted of a laser light source and collecting lens for collecting and irradiating laser light onto the minute particles P, a dichroic mirror, a bandpass filter, and the like, and a detection system 32 (detection means 32) that collects measurement target light generated from the minute particles P by the irradiation of the laser light in a detector 33 (detection means 33). The detector 33 may be constituted of, for example, an area image pickup device such as a PMT (Photo Multiplier Tube), a CCD, and a CMOS. It should be noted that although the irradiation system and the collecting system are structured separately in the figure, the irradiation system and the collecting system may have structures in which they have a common optical path.

The measurement target light detected by the detector 33 is light that is generated from the minute particles P by the irradiation of the laser light, and forward-scattered light or side-scattered light, scattered light of Rayleigh scattering, Mie scattering, or the like, and fluorescent light can be used, for example. The measurement target light is converted into an electric detection signal and output to a controller 4. The controller 4 calculates the flow sending interval of the minute particles P in the flow path 11 based on the detection signal and controls the oscillation frequency of the oscillation device 112 based on the calculated flow sending interval.

By oscillating the oscillation device 112 at a predetermined oscillation frequency based on the flow sending interval of the minute particles P in the flow path 11, control can be performed to incorporate a predetermined number of minute particles P in the droplet A discharged from the orifice 111. FIG. 5 has shown the example where control is performed to incorporate one minute particle P in the droplet A. By controlling the oscillation frequency based on the flow sending interval, it also becomes possible to incorporate two or more minute particles in the droplet or incorporate different numbers of minute particles in the droplet, for example.

It should be noted that the detection means 31, 32, and 33 may be replaced by, for example, an electric or magnetic detection means. When electrically or magnetically detecting minute particles, minute electrodes are oppositely provided on both sides of the flow path 11, and a resistance value, a capacitance value, an inductance value, an impedance, and a change value of an electric field between the electrodes, or a magnetization, a magnetic field change, and the like are measured.

It should be noted that although FIGS. 3 to 5 have shown the example where the droplets A including the minute particles are discharged from the orifice 111 of the flow path 11, the fluid including the minute particles may flow through two or more flow paths. For example, it is also possible to cause a fluid including minute particles to also flow through the flow path 12 in addition to the flow path 11 and discharge droplets A and B including the minute particles from the orifices 111 and 121. In this case, by generating the droplet G (see FIG. 3) or droplet H (see FIG. 4) by causing the droplets A, B, and C to collide with one another, the minute particles included in the droplets A and B and the substance included in C are mixed. Either of the fluids flowing through the flow paths 11 and 12 may include minute particles of one type or two types or more, or the minute particles may either be the same or different.

3. Dispense of Mixed Droplets (3-1) Dispense by Charge Means

Figure 6:
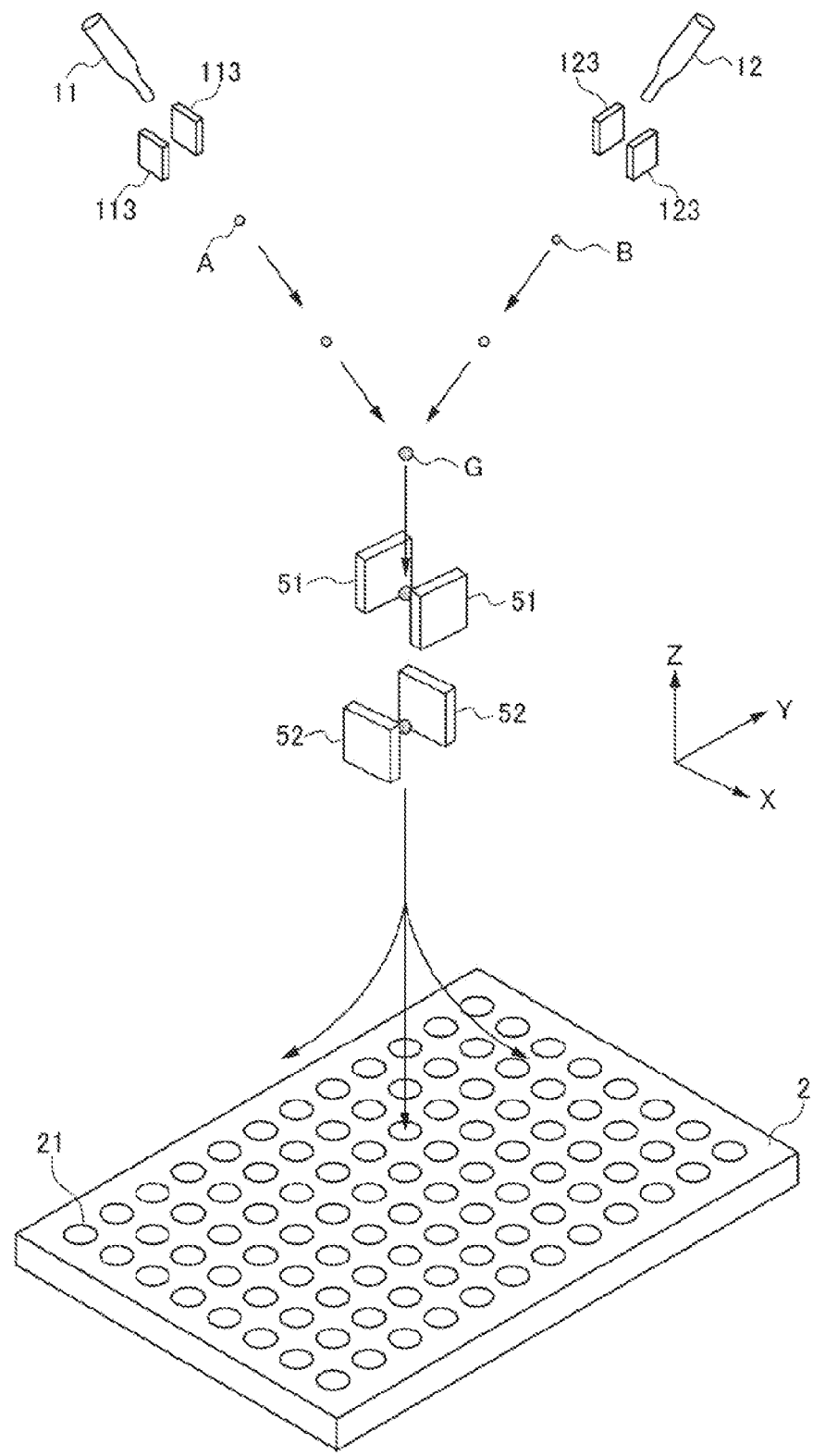
FIG. 6 A diagram for explaining a structure for dispensing mixed droplets in the substance mixing apparatus according to the first embodiment.

FIG. 6 is a schematic diagram for explaining a structure for dispensing the collided/mixed droplet G in the substance mixing apparatus according to the first embodiment. The figure shows a structure for dispensing the droplet G to a plurality of areas by controlling a movement direction of the droplet G using an electric action force. In the figure, the reference numeral 21 denotes each of the plurality of areas formed in the vessel 2.

The droplets A and B discharged from the flow paths 11 and 12 collide with each other to become a droplet G which flies according to an inertia of the droplets A and B. In the figure, the reference numerals 51, 51 denote first paired electrodes provided oppositely along the movement direction of the droplet G. Further, the reference numerals 52, 52 denote second paired electrodes similarly provided oppositely along the movement direction of the droplet G. The first paired electrodes 51, 51 and the second paired electrodes 52, 52 are provided such that opposite axes thereof become orthogonal to each other. In other words, the first paired electrodes 51, 51 are opposed in the X-axis direction in the figure, and the second paired electrodes 52, 52 are opposed in the Y-axis direction.

On the other hand, in the figure, the reference numerals 113, 113 denote a charge means for charging the droplets A discharged from the flow path 11 and imparting a charge. Further, the reference numerals 123, 123 denote a charge means for similarly imparting a charge to the droplets B discharged from the flow path 12. Here, the case where the charge means are structured as the paired electrodes provided along the discharge direction of the droplets A and B has been shown. However, the structure of the charge means is not particularly limited as long as it is capable of imparting a charge to the droplets A and B. As an example of other structures of the charge means, there is a structure in which a metal member is provided so as to come into contact with the fluids flowing through the flow paths 11 and 12, and a voltage is imparted to the metal member.

Either one or both of the droplets A and B discharged from the flow paths 11 and 12 can be imparted with a positive or negative charge to positively or negatively charge the droplet G obtained after the collision. Then, by the charge imparted to the droplet G and an electric repulsion force or absorption force that acts between the first paired electrodes 51, 51, the movement direction of the droplet G that passes the first paired electrodes 51, 51 is controlled in positive and negative directions along the X axis. Furthermore, by the charge imparted to the droplet G and an electric force that acts between the second paired electrodes 52, 52, the movement direction of the droplet G that passes the second paired electrodes 52, 52 is controlled in positive and negative directions along the Y axis.

The flying direction of the droplet G that has passed the second paired electrodes 52, 52 can be arbitrarily controlled in the X- and Y-axis directions in the figure by varying a voltage applied to the first paired electrodes 51, 51 and the second paired electrodes 52, 52 and adjusting an intensity of the electric action force between the droplet G. Accordingly, the droplet G can be guided to the plurality of areas 21 formed in the vessel 2 so that the droplet G is retrieved in the areas. 0 or 1 or more droplet G can be guided to and retrieved in each of the areas 21. It should be noted that control of the flying direction of the droplet G can be adjusted by varying the charge imparted to the droplet A or B by the charge means 113, 113 or 123, 123.

A fluid including minute particles can be caused to flow through the flow paths so that droplets including the minute particles are discharged from the orifices, and by oscillating the oscillation device 112 at a predetermined oscillation frequency based on the flow sending interval of the minute particles P in the flow path 11, for example, control can be performed such that a predetermined number of minute particles P are incorporated in the droplet A discharged from the orifice 111 (see FIG. 5). In this case, it is also possible to incorporate a predetermined number of minute particles P in the droplet G obtained after the collision of the droplet A and dispense a certain number of minute particles to the plurality of areas 21 by guiding the droplet G to each of the areas 21 formed in the vessel 2 for retrieval. The number of minute particles to be incorporated in the droplet is not particularly limited and can be set arbitrarily, but by dispensing the droplets each including one cell as a minute particle one each to the areas, for example, it can be used for pharmacokinetics studies that uses single-cell screening.

(3-2) Dispense by Drive Means

Figure 7:
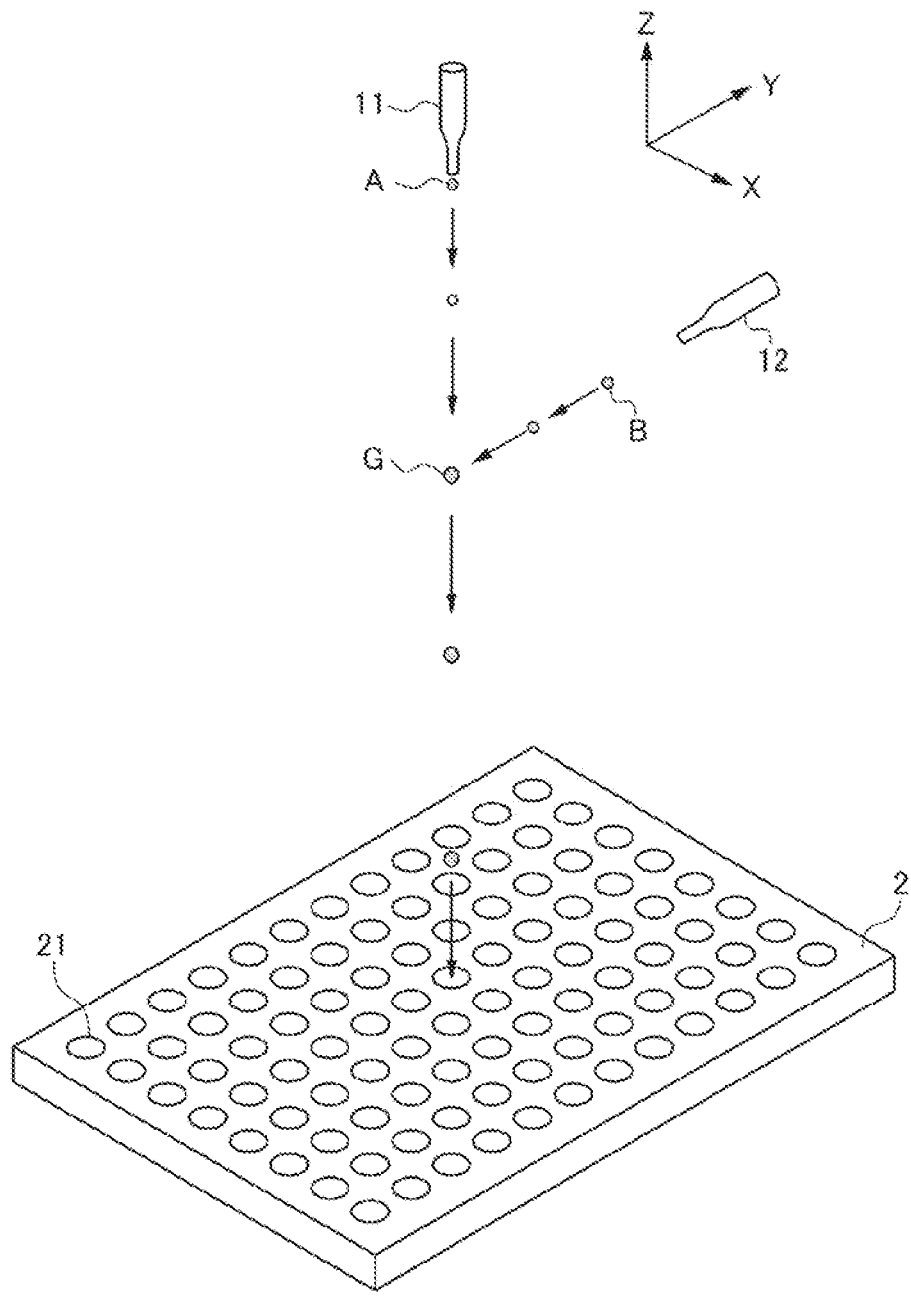
FIG. 7 A diagram for explaining the structure for dispensing mixed droplets in the substance mixing apparatus according to the modified example of the first embodiment.

FIG. 7 is a schematic diagram for explaining a structure for dispensing the droplet G obtained after the collision and mixing in the substance mixing apparatus according to a modified example of the first embodiment. The figure shows a structure for dispensing the droplet G to the plurality of areas 21 of the vessel 2 by moving the flow paths by the drive means.

Relative positions of the flow paths 11 and 12 with respect to the vessel 2 can be changed in the X- and Y- axis directions in the figure by a drive means (not shown). The drive means is not particularly limited as long as it can move the relative positions of the flow paths 11 and 12 with respect to the vessel 2 and can be constituted of, for example, a feed screw, a guide, and a motor.

By arbitrarily controlling the flying direction of the droplet G in the X- and Y- axis directions in the figure by sequentially varying the relative positions of the flow paths 11 and 12 with respect to the vessel 2 by the drive means, 0 or 1 or more droplet G can be retrieved in each of the plurality of areas 21 formed in the vessel 2. It should be noted that the number of droplets G to be retrieved in the areas 21 may all be the same or may be different.

It should be noted that FIGS. 6 and 7 have shown the case where a multi-plate in which 96 wells (areas 21) are formed on a plastic substrate is used as the vessel 2. Various plastic vessels that are normally used may also be used as the vessel 2, and by providing a plurality of those, 0 or 1 or more droplet G can be guided to and retrieved in each of the vessels 2.

Figure 8:
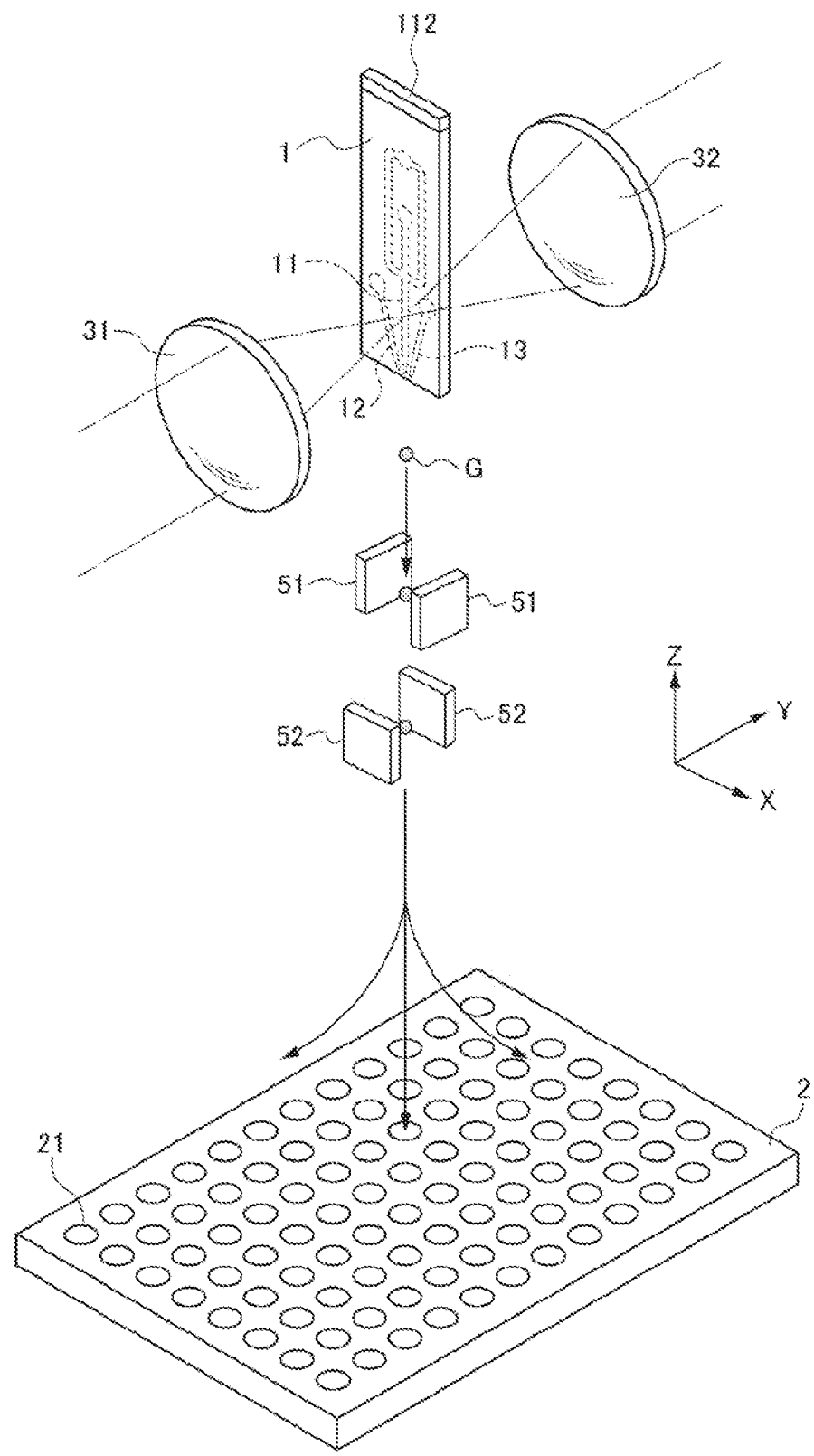
FIG. 8 A diagram for explaining a third embodiment of the substance mixing apparatus according to the present invention.

4. Microchip-Type Substance Mixing Apparatus (4-1) General Overview of Apparatus Structure FIG. 8 is a schematic diagram for explaining a third embodiment of the substance mixing apparatus according to the present invention. The substance mixing apparatus of this embodiment has characteristics that the flow paths through which fluids including substances to be mixed flow are formed on a single microchip. The figure shows a schematic structure of the apparatus.

In the figure, the reference numeral 1 denotes a microchip. On the microchip 1, the flow paths 11, 12, and 13 through which fluids including substances to be mixed flow are formed. Of those, a fluid including minute particles flows through the flow path 11.

The reference numeral 112 denotes an oscillation device for forming droplets of the fluids discharged from the orifices of the flow paths 11, 12, and 13 and discharging them. Here, an internal structure of the chip in which the oscillation device 112 is integrally formed with the microchip 1 will be described, but it is also possible for the oscillation device 112 to be provided on the apparatus main body side at a position where it comes into contact with the chip when the chip is mounted to the apparatus.

Further, the reference numerals 31 and 32 denote a detection means for detecting the minute particles included in the fluid that flows through the flow path 11, the detection means being an irradiation system and a detection system (also see FIG. 5).

The fluid including substances to be mixed is fed to the flow paths 11, 12, and 13 by a fluid feeding means (not shown) and discharged as droplets from the orifices of the flow paths by the function of the oscillation device 112. The discharged droplet collides at a predetermined position in a space outside the microchip 1 to become a single droplet G, with the result that the substances are mixed (also see FIG. 3). Further, the movement direction of the droplet G obtained after the collision is controlled by the first paired electrodes 51, 51 and the second paired electrodes 52, 52 so that the droplet G is guided to and retrieved in the plurality of areas 21 formed in the vessel 2 (also see FIG. 6).

The microchip 1 may be formed of glass or various plastics (PP, PC, COP, PDMS, etc.). It is desirable for the material of the microchip to have permeability with respect to laser light irradiated by the detection means 31 and have less optical errors due to small autogenous fluorescence and a small wavelength dispersion.

The formation of the flow path 11 and the like on the microchip 1 can be carried out by wet etching or dry etching of a glass substrate, or nanoimprint, injection molding, and mechanical processing of a plastic substrate. The microchip 1 can be formed by sealing a substrate on which the flow path 11 and the like are formed with a substrate formed of the same material or a different material.

(4-2) Microchip

Figure 9:
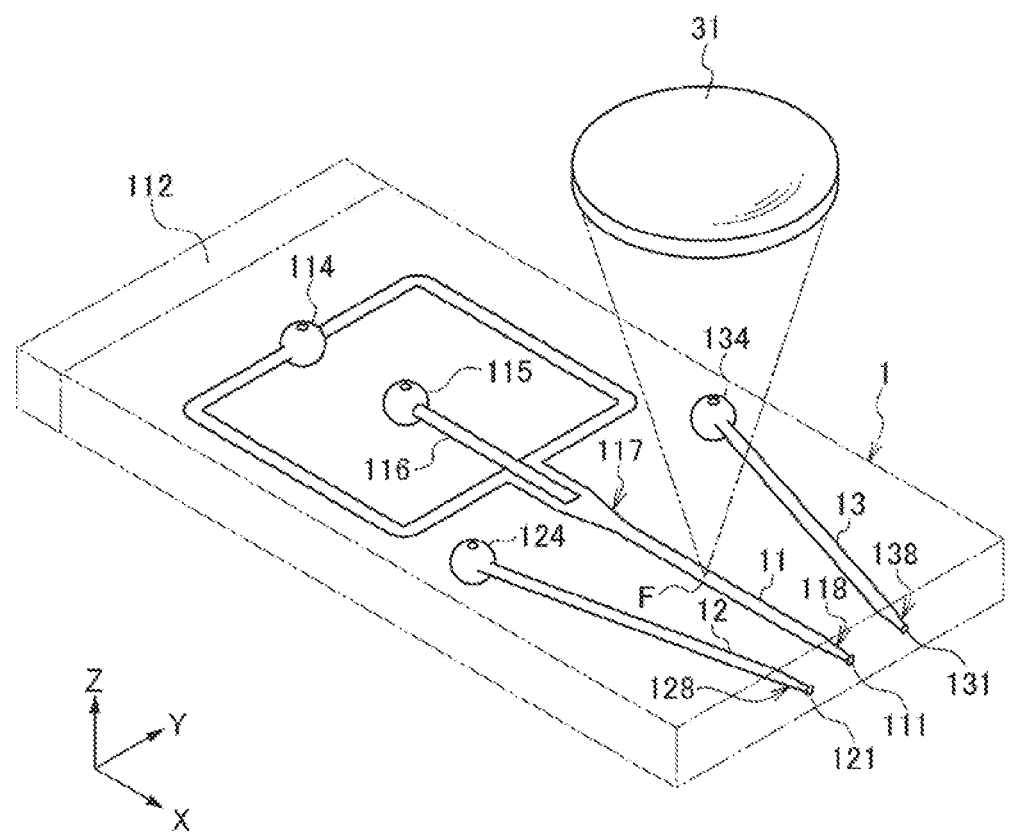
FIG. 9 A diagram for explaining a microchip according to the present invention.

Referring to FIG. 9, the structure of the microchip 1 will be described in detail.

On the microchip 1, a sample fluid inlet 115 into which a fluid including minute particles to be mixed (hereinafter, referred to as "sample fluid") is introduced and a sheath fluid inlet 114 into which a sheath fluid is introduced are formed. The sample fluid introduced into the sample fluid inlet 115 flows through a minute pipe 116 to be fed to the flow path 11. Further, the sheath fluid introduced into the sheath fluid inlet 114 first splits bidirectionally in the positive and negative directions on the Y axis from the sheath fluid inlet 114 to be fed, and then turns twice at almost 90 degrees to join at the position where the minute pipe 116 is provided.

The minute pipe 116 introduces the sample fluid that has been introduced from the sample fluid inlet 115 into a sheath fluid laminar flow flowing through the flow path 11 after the confluence. Accordingly, the minute pipe 116 feeds the sample fluid downstream of the flow path 11 while the sample fluid laminar flow is surrounded by the sheath fluid laminar flow. By feeding the sample fluid laminar flow to the center of the sheath fluid laminar flow, minute particles in the sample fluid laminar flow can be fed while being aligned in one line in the flow path 11.

The detection means (indicating only irradiation system 31 in figure) irradiates laser light onto the minute particles flowing through the flow path 11 in a line, detects measurement target light generated from the minute particles, and converts it into an electric detection signal. Hereinafter, a part where the detection of minute particles is carried out in the flow path 11 will be referred to as "detection portion" (denoted by symbol F in figure). The sample fluid and sheath fluid that have passed the detection portion F are discharged outside the flow path 11 from the orifice 111 opened at one side of the microchip 1.

Figure 10:
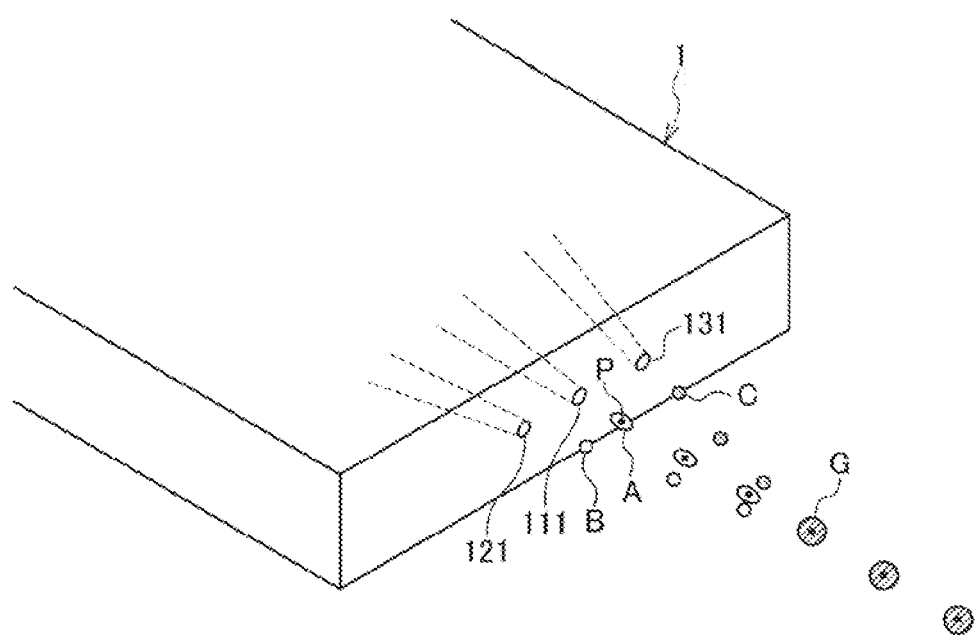
FIG. 10 A diagram schematically showing droplets discharged from the microchip according to the present invention.

The detection signal from the detection means is output to the controller 4 (not shown) which calculates the flow sending interval of the minute particles in the flow path 11 based on the detection signal and controls the oscillation frequency of the oscillation device 112 based on the calculated flow sending interval (also see FIG. 5). Then, by oscillating the microchip 1 at a predetermined oscillation frequency based on the flow sending interval of the minute particles, the oscillation device 112 forms droplets of the sample fluid and sheath fluid discharged from the orifice 111 and controls to incorporate a predetermined number of minute particles in the droplets. FIG. 10 shows a case where control is performed to incorporate one minute particle P in the droplet A discharged from the orifice 111. It is also possible to incorporate two or more minute particles in each droplet or incorporate different numbers of minute particles in the droplets.

It should be noted that the detection means may be replaced by, for example, an electric or magnetic detection means as already described above. When electrically or magnetically detecting minute particles, minute electrodes are oppositely provided on both sides of the flow path 11, and a resistance value, a capacitance value, an inductance value, an impedance, and a change value of an electric field between the electrodes, or a magnetization, a magnetic field change, and the like are measured.

Moreover, on the microchip 1, inlets 124 and 134 into which fluids including substances to be mixed are introduced are formed. The fluids introduced into the flow paths 12 and 13 via the inlets 124 and 134 are also discharged as droplets B and C from the orifices 121 and 131 by the oscillation of the oscillation device 112.

The orifice 111 of the flow path 11, the orifice 121 of the flow path 12, and the orifice 131 of the flow path 131 are opened on the same side of the microchip 1 and provided such that the droplets A, B, and C discharged from the orifices of the flow paths can collide with one another. Specifically, as described with reference to FIG. 3, the collision angle $\theta_{12}$ of the droplets A and B, the collision angle $\theta_{13}$ of the droplets A and C, and the flying distances $L_{11}$, $L_{12}$, and $L_{13}$ to the collision positions of the droplets are set as appropriate based on the flying speed and size of the droplets, the discharge interval from the orifices, and the like to enable the droplets to collide with one another.

In the substance mixing apparatus, the fluid including the minute particles P is discharged as the droplets A from the orifice 111 of the flow path 11 and the fluids including substances to be mixed are discharged as the droplets B and C from the orifices 121 and 131 of the flow paths 12 and 13. By causing those droplets to collide with one another, the minute particles and substances included in the droplets can be uniformly mixed within a short time.

Further, in the substance mixing apparatus, by adjusting the fluid feeding amount (flow rate) with respect to the flow paths 12 and 13, the diameters of the orifices 121 and 131, and the like, the sizes of the droplets A, B, and C can be adjusted and the substances can be incorporated into the droplets in a certain amount. Therefore, the plurality of substances can be mixed with the minute particles P without causing variances in the amounts.

Furthermore, in the substance mixing apparatus, since the flow paths 11, 12, and 13 are formed on a single microchip 1, positioning (alignment) of the flow paths and the orifices to enable the droplets to collide with one another do not need to be carried out. Moreover, by using an inexpensive microchip that can be used disposably as means for forming droplets and means for causing the droplets to collide with one another, it becomes possible to prevent contamination from occurring among analysis samples.

FIGS. 9 and 10 have shown the case where substances are mixed by providing three flow paths 11, 12, and 13. However, the number of flow paths to be provided in the microchip 1 is not particularly limited and may be 4 or more. Moreover, the collision angle $\theta_{12}$ of the droplets A and B, the collision angle $\theta_{13}$ of the droplets A and C, and the flying distances $L_{11}$, $L_{12}$, and $L_{13}$ to the collision positions of the droplets can be set arbitrarily within the range in which the droplets are capable of colliding with one another, and along with that, the setting positions of the flow paths 11, 12, and 13 and orifices 111, 121, and 131, and the like on the microchip 1 can be changed as appropriate.

Furthermore, although FIGS. 9 and 10 have shown the example of a case where the droplets A including minute particles are discharged from the orifice 111 of the flow path 11, the fluid including minute particles may be caused to flow through two or more flow paths. For example, it is also possible to provide the sheath fluid inlet, the minute pipe, the detection portion F, and the like in the flow path 12 as in the flow path 11 and discharge the droplets A and B including the minute particles from the orifices 111 and 121. In this case, both of the fluids flowing through the flow paths 11 and 12 may include one type or two or more types of minute particles, and the minute particles included in the fluids may either be the same or different.

Hereinafter, with reference to FIGS. 11 to 14 in addition to FIG. 9, the structure of the microchip 1 will be described in more detail.

In FIG. 9, the reference numeral 117 denotes a narrowing portion provided in the flow path 11. The narrowing portion 117 is formed such that the vertical cross-sectional area with respect to the fluid feeding direction gradually becomes smaller from the upstream side to the downstream side in the flow path.

Figure 11:
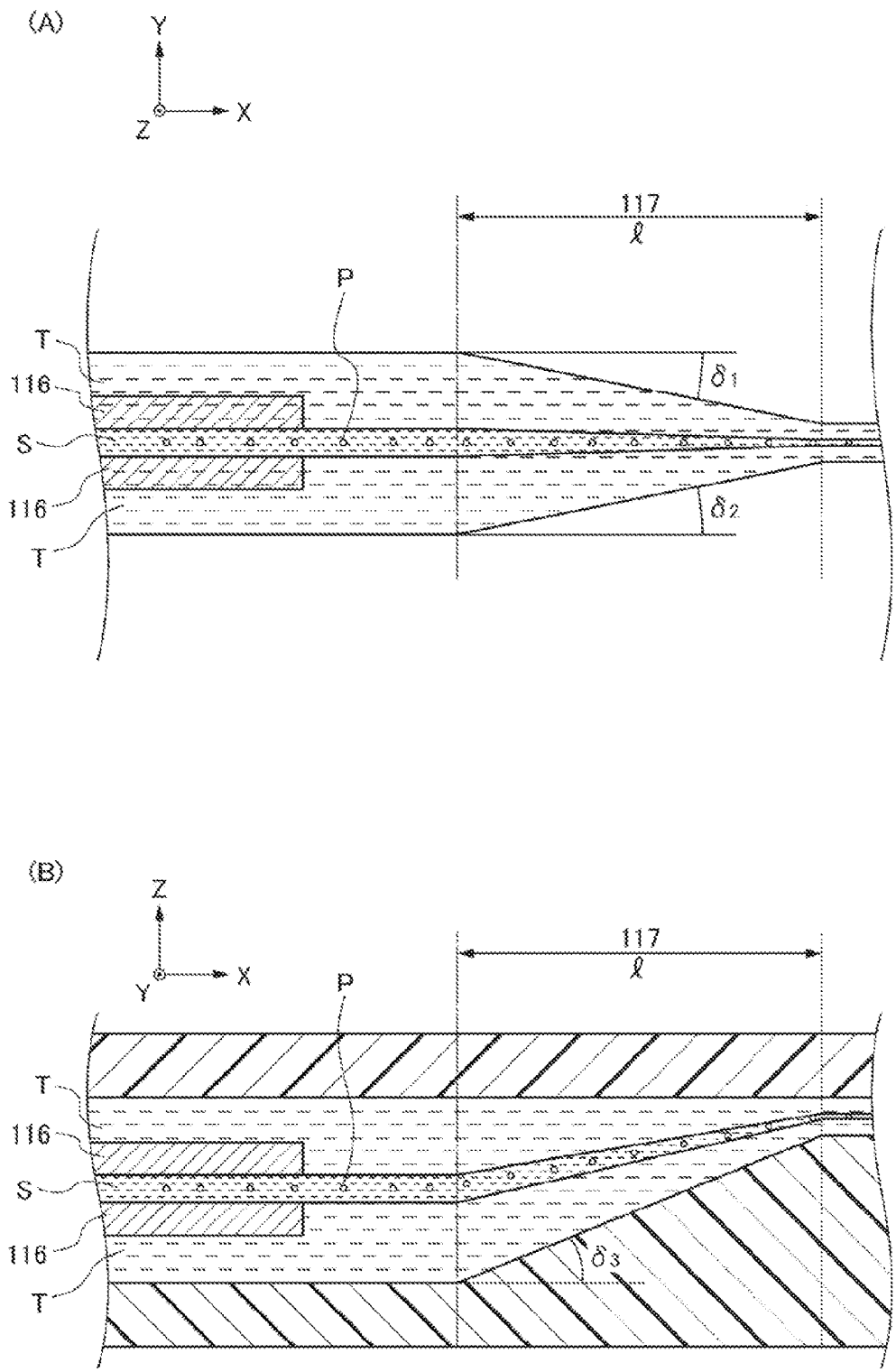
FIG. 11 Diagrams for explaining a setting position of a minute pipe 116, a structure of a flow path 11 in the vicinity of a narrowing portion 117, and states of a flowing sample fluid laminar flow and sheath fluid laminar flow.

FIG. 11 are schematic cross-sectional diagrams for explaining the setting position of the minute pipe 116, the structure of the flow path 11 in the vicinity of the narrowing portion 117, and states of the flowing sample fluid laminar flow and sheath fluid laminar flow. FIG. 11(A) shows a horizontal cross-sectional diagram (XY cross-sectional diagram), and FIG. 11(B) shows a vertical cross-sectional diagram (ZX cross-sectional diagram). In the figures, the symbol S decodes the sample fluid laminar flow, the symbol T decodes the sheath fluid laminar flow, and the symbol P decodes minute particles included in the sample fluid.

The sample fluid laminar flow S is introduced into the sheath fluid laminar flow T flowing through the flow path 11 via the minute pipe 116 and fed while surrounded by the sheath fluid laminar flow T (3D laminar flow) as shown in the figures.

A flow path side wall of the narrowing portion 117 is formed to narrow in the fluid feeding direction along the Y-axis direction in the figure, and the narrowing portion 117 is of a cone shape that gradually narrows in an upper view. By this shape, the narrowing portion 117 narrows a laminar flow width of the sheath fluid and the sample fluid and feeds them. Moreover, the narrowing portion 117 is formed to be an inclined surface whose flow path bottom surface becomes higher in a depth direction (Z-axis direction) from the upstream side to the downstream side and also narrows the laminar flow width in the same direction.

As described above, by forming the 3D laminar flow in which the sample fluid laminar flow S is surrounded by the sheath fluid laminar flow T and narrowing the laminar flow width of the 3D laminar flow to feed it, the minute particles P can be arranged one by one in the narrowed sample fluid laminar flow S. As a result, a flow sending position of the minute particles P in the flow path 11 can be positioned, and laser light from the detection means 31 can be accurately irradiated onto the minute particles P in the detection portion F.

In particular, since the laminar flow width of the sample fluid laminar flow S can be narrowed in not only the horizontal direction of the microchip 1 (Y-axis direction in FIG. 11(A)) but also the vertical direction (Z-axis direction in FIG. 11(B)) by the narrowing portion 117, a focal position of the laser light in the depth direction of the flow path 11 can be made to accurately match the flow sending position of the minute particles P. Therefore, it becomes possible to obtain a high measurement sensitivity by accurately irradiating laser light onto the minute particles P.

Here, it is considered that, by forming the flow path 11 as a sufficiently-thin flow path and introducing the sample fluid laminar flow S into the sheath fluid laminar flow T flowing through the flow path 11 using the minute pipe 116 having a small diameter, it is possible to form a 3D laminar flow in which the laminar flow width is narrowed in advance. In this case, however, by making the diameter of the minute pipe 116 small, there is a possibility that the minute particles P might get stuck in the minute pipe 116.

By providing the narrowing portion 117 in the microchip 1, it is possible to narrow down the laminar flow width after the 3D laminar flow is formed using the minute pipe 116 having a sufficiently-larger diameter than the diameter of the minute particles P included in the sample fluid. Therefore, the problem of the minute pipe 116 getting stuck is not caused.

FIG. 11 have shown the case where the minute pipe 116 is provided such that the center thereof becomes coaxial with the center of the flow path 11. In this case, the sample fluid laminar flow S is introduced into the center of the sheath fluid laminar flow T flowing through the flow path 11. The position of the sample fluid laminar flow S in the sheath fluid laminar flow T can be set arbitrarily by adjusting the opening position of the minute pipe 116 in the flow path 11. Moreover, for narrowing down the laminar flow width, the narrowing portion 117 only needs to be formed such that the area of the vertical cross section with respect to the fluid feeding direction gradually decreases from the upstream side to the downstream side in the flow path. Without being limited to the shape shown in FIG. 11, the narrowing portion 117 can be formed such that, for example, both the flow path bottom surface and upper surface are formed as inclined surfaces so that narrowing down can be performed.

The inner diameter of the minute pipe 116 can be set as appropriate based on the diameter of the minute particles P. For example, when carrying out a reaction analysis with blood cells using blood as the sample fluid, the inner diameter of the minute pipe 116 is favorably about 10 to 500 μm. Further, the width and depth of the flow path 11 at the opening position of the minute pipe 116 only need to be set as appropriate based on the outer diameter of the minute pipe 116 onto which the diameter of the minute particles P is reflected. For example, when the inner diameter of the minute pipe 116 is about 10 to 500 μm, the width and depth of the flow path 11 at the opening position of the minute pipe 116 are favorably about 100 to 2000 μm. It should be noted that the cross-sectional shape of the minute pipe may be an arbitrary shape such as an oval, a square, and a triangle instead of a circle.

The laminar flow width of the sample fluid laminar flow S and the sheath fluid laminar flow T that has been narrowed down by the narrowing portion 117 can be narrowed down to an arbitrary laminar flow width by appropriately adjusting the vertical cross-sectional area of the narrowing portion 117 with respect to the fluid feeding direction. For example, when a flow path length of the narrowing portion 17 is represented by l and an inclination angle of the flow path bottom surface is represented by $\delta_3$ in FIG. 11(B), the narrowing width of the 3D laminar flow at the narrowing portion 17 becomes l*tan $\delta_3$. Therefore, by adjusting the flow path length l and the inclination angle $\delta_3$ as appropriate, an arbitrary narrowing width can be set. Furthermore, with narrowing angles of the flow path side wall of the narrowing portion 117 in the Y-axis direction being represented by $\delta_1$ and $\delta_2$ which satisfy, together with $\delta_3$, "$\delta_3=2*\delta_1$, $\delta_1=\delta_2$" in FIG. 11(A), the sample fluid laminar flow S and the sheath fluid laminar flow T can be contracted isotropically, and the laminar flow width can be narrowed down without disturbing the 3D laminar flow formed by the minute pipe 116.

The laminar flow width of the sample fluid laminar flow S and the sheath fluid laminar flow T at the detection portion F, that has been narrowed by the narrowing portion 117, is favorably about 20 to 2000 μm in width and depth of the flow path 11.

In FIG. 9, the reference numeral 118 denotes a pressor portion that is provided in the flow path 11 at a position upstream from the orifice 111 and downstream from the detection portion F. The pressor portion 118 is formed such that the vertical cross-sectional area with respect to the fluid feeding direction gradually decreases from the upstream side to the downstream side in the flow path. In other words, similar to the narrowing portion 117, the pressor portion 118 is formed such that the flow path side wall narrows in the Y-axis direction in the figure along the fluid feeding direction and the flow path bottom surface becomes an inclined surface that becomes higher in the depth direction (Z-axis direction) from the upstream side to the downstream side.

Figure 12:
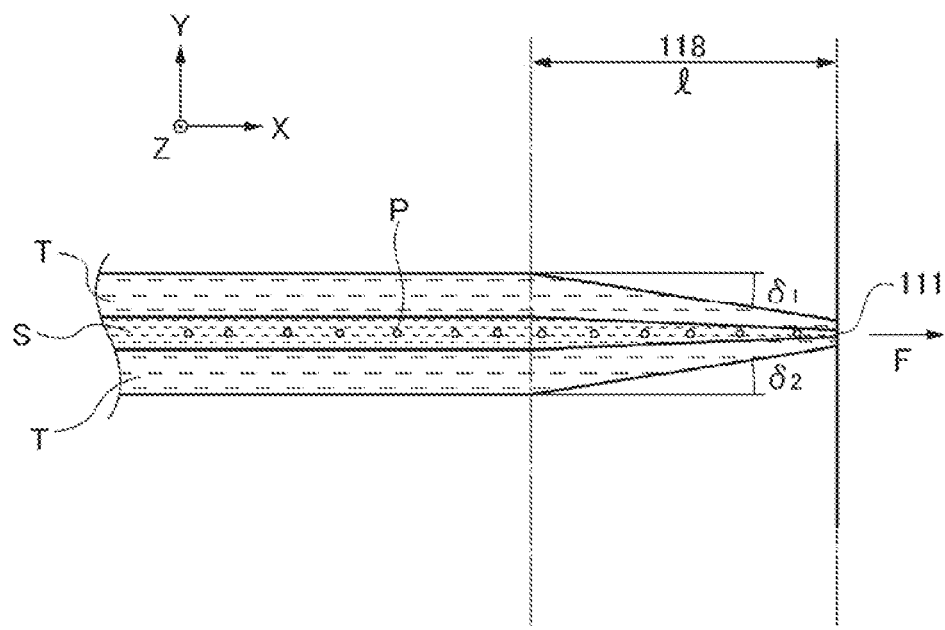
FIG. 12 Diagrams for explaining structures of a pressor portion 118 and the flow path 11 in the vicinity of an orifice 111, and states of the flowing sample fluid laminar flow and sheath fluid laminar flow.
Figure 12:
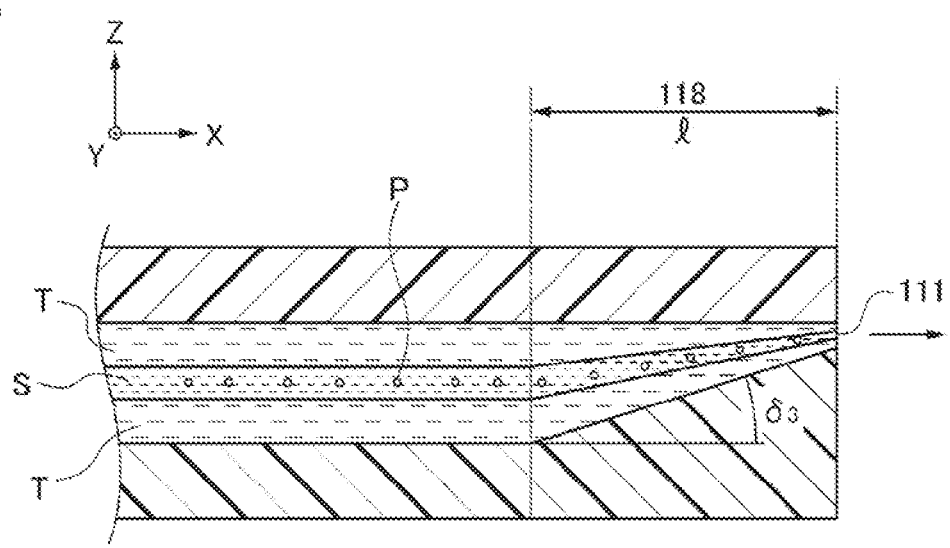

FIG. 12 are schematic cross-sectional diagrams for explaining the structures of the pressor portion 118 and the flow path 11 in the vicinity of the orifice 111, and the states of the flowing sample fluid laminar flow and sheath fluid laminar flow. FIG. 12(A) shows a horizontal cross-sectional diagram (XY cross-sectional diagram), and FIG. 12(B) shows a vertical cross-sectional diagram (ZX cross-sectional diagram). In the figures, the symbol S decodes the sample fluid laminar flow, the symbol T decodes the sheath fluid laminar flow, and the symbol P decodes minute particles included in the sample fluid.

The sample fluid laminar flow S and the sheath fluid laminar flow T are fed while the laminar flow width is narrowed down by the pressor portion 118 in the Y- and Z-axis directions in the figure. By the narrowing of the laminar flow width, the pressor portion 118 functions to increase a fluid feeding pressure of the sample fluid and the sheath fluid in the flow path 11 and discharging the fluids from the orifice 111 at a high pressure.

The laminar flow width of the sample fluid laminar flow S and the sheath fluid laminar flow T at the orifice 111 part can be narrowed down to an arbitrary laminar flow width by appropriately adjusting the vertical cross-sectional area of the pressor portion 118 with respect to the fluid feeding direction. For example, when the flow path length of the pressor portion 118 is represented by l and the inclination angle of the flow path bottom surface is represented by $\delta_3$ in FIG. 12(B), the narrowing width of the 3D laminar flow at the pressor portion 118 becomes l*tan $\delta_3$. Therefore, an arbitrary narrowing width can be set by adjusting the flow path length l and the inclination angle $\delta_3$ as appropriate. The laminar flow width of the sample fluid laminar flow S and the sheath fluid laminar flow T at the orifice 111 part is favorably about 20 to 500 μm in width and depth of the orifice 111 part.

It should be noted that the pressor portion 118 is the same as the narrowing portion 117 in the point that the narrowing of the laminar flow width of the sample fluid laminar flow S and the sheath fluid laminar flow T can be carried out with both the flow path bottom surface and upper surface of the pressor portion 118 as inclined surfaces and the shape of the pressor portion 118 is not limited to the shape shown in the figures. Furthermore, with narrowing angles of the flow path side wall of the pressor portion 118 in the Y-axis direction being represented by $\delta_1$ and $\delta_2$ which satisfy, together with the narrowing angle $\delta_3$ in the Z-axis direction, "$\delta_3=2*\delta_1$, $\delta_1=\delta_2$" in FIG. 12(A), the 3D laminar flow formed by the minute pipe 116 can be contracted isotropically, and the laminar flow width can be narrowed down without disturbing the 3D laminar flow as described above with respect to the narrowing portion 117.

Similar to the pressor portion 118 of the flow path 11, pressor portions 128 and 138 are provided in the flow paths 12 and 13 for discharging fluids from the orifices 121 and 131 at a high pressure. The flow path width and depth at the orifice 121, 131 parts can be narrowed down to an arbitrary system by appropriately adjusting the vertical cross-sectional areas of the pressor portions 128 and 138 with respect to the fluid feeding direction. By adjusting the diameters of the orifices 121 and 131 and the like, it is possible to adjust sizes of the droplets B and C and adjust the amount of substances to be mixed with the droplet A.

Figure 13:
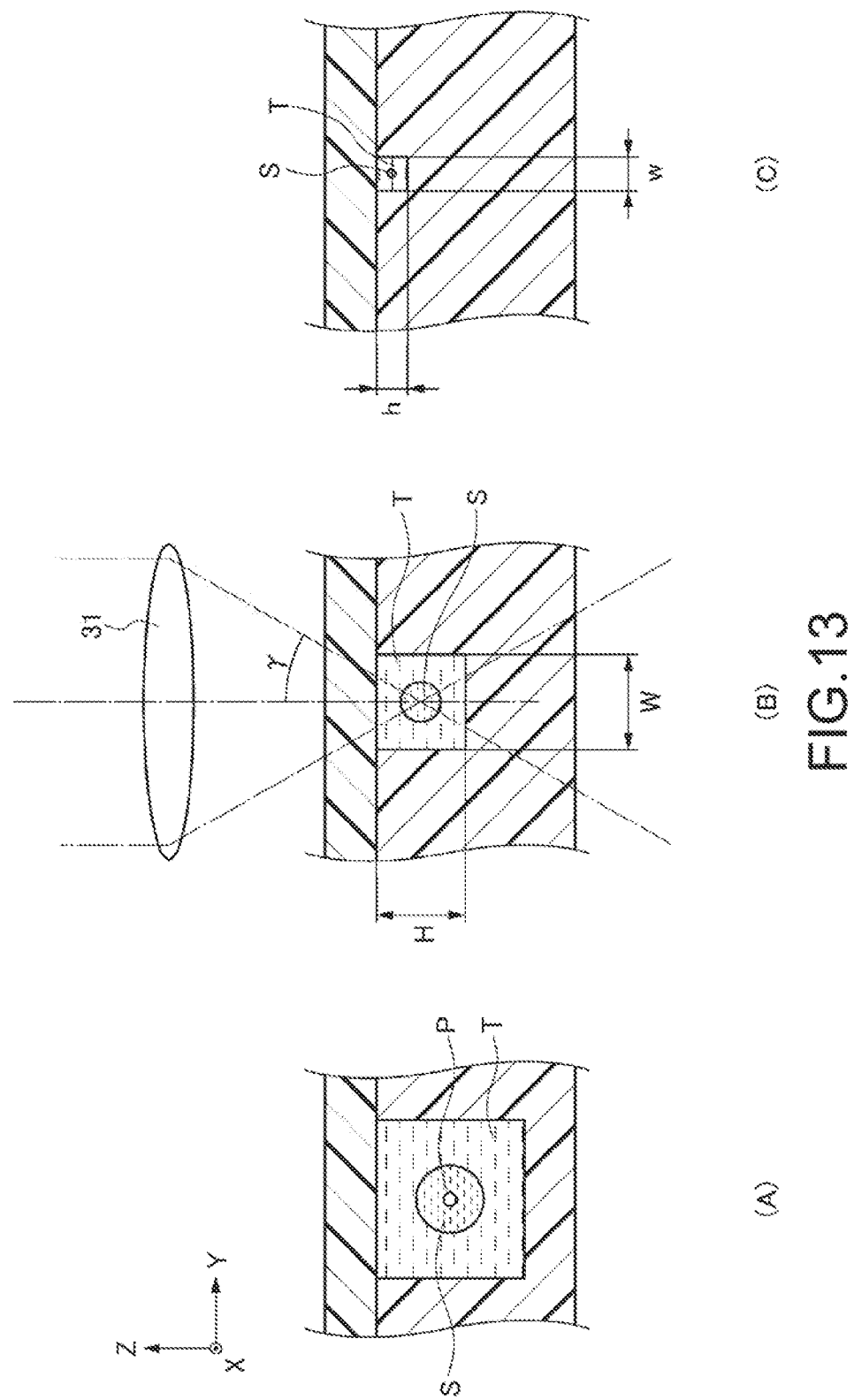
FIG. 13 Diagrams for explaining a width and depth of the flow path 11 at respective portions.

FIG. 13 are schematic cross-sectional diagrams for explaining the widths and depths at respective parts of the flow path 11. The figures each show a YZ cross section of the flow path 11. FIG. 13(A) shows a cross section of the opening position of the minute pipe 116, FIG. 13(B) shows a cross section of the detection portion F, and FIG. 13(C) shows a cross section of the orifice 111 part of the flow path 11.

As shown in FIG. 13(A), at the opening position of the minute pipe 116, the sample fluid laminar flow S and the sheath fluid laminar flow T are fed as the 3D laminar flow in which the sample fluid laminar flow S is surrounded by the sheath fluid laminar flow T. As already described above, the width and depth of the flow path 11 at the opening position of the minute pipe 116 are set as appropriate to, for example, about 100 to 2000 μm based on the outer diameter of the minute pipe 116 onto which the diameter of the minute particles P is reflected.

The 3D laminar flow formed by the minute pipe 116 is fed to the detection portion F in a state where the laminar flow width is narrowed down by the narrowing portion 117 (see FIG. 13(B)). By narrowing down the laminar flow width by the narrowing portion 117, the minute particles P are arranged one by one in the sample fluid laminar flow S to be fed to the detection portion F.

The laminar flow width of the sample fluid laminar flow S and the sheath fluid laminar flow T at the detection portion F can be set as appropriate by appropriately adjusting the vertical cross-sectional area of the narrowing portion 117 with respect to the fluid feeding direction. The width (W) and depth (H) of the flow path 11 at the detection portion F are set to be about 20 to 2000 μm for making an optical detection angle (numerical aperture of optical system) of the detection means 31 sufficiently large. As a result, an optical detection angle γ and the numerical aperture can be made sufficiently large.

Furthermore, the shape of the flow path 11 at the light irradiation portion 33 is favorably a rectangle with respect to an irradiation direction of measurement light irradiated by a light detection means 3 with an increased width (W) with respect to the depth (H). With such a broad shape of the flow path 11 at the light irradiation portion 33, it is possible to increase the numerical aperture of the optical system.

The sample fluid laminar flow S and the sheath fluid laminar flow T that have passed the detection portion F are fed to the orifice 111 after the laminar flow width is again narrowed down by the pressor portion 118 as shown in FIG. 13(C). By narrowing down the laminar flow width by the pressor portion 118, a discharge pressure of the sample fluid and sheath fluid from the orifice 111 can be increased.

The laminar flow width of the sample fluid laminar flow S and the sheath fluid laminar flow T at the orifice 111 part can be set arbitrarily by appropriately adjusting the vertical cross-sectional area of the pressor portion 118 with respect to the fluid feeding direction. For forming high-frequency droplets at a high speed at the orifice 111, it is favorable to make the laminar flow width of the sample fluid laminar flow S and the sheath fluid laminar flow T at the orifice 111 part small to thus sufficiently increase the discharge pressure of the sample fluid and the sheath fluid. Therefore, the width (w) and depth (h) of the flow path 11 at the opening of the orifice 111 are favorably set to be about 20 to 500 μm.

Figure 14:
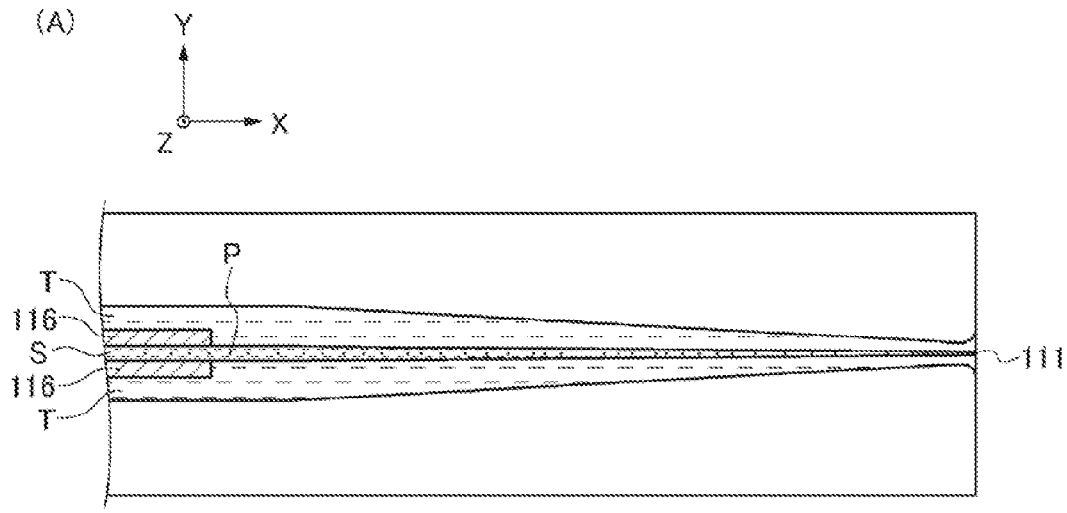
FIG. 14 Diagrams for explaining other favorable embodiments on the width and depth of the flow path 11.
Figure 14:
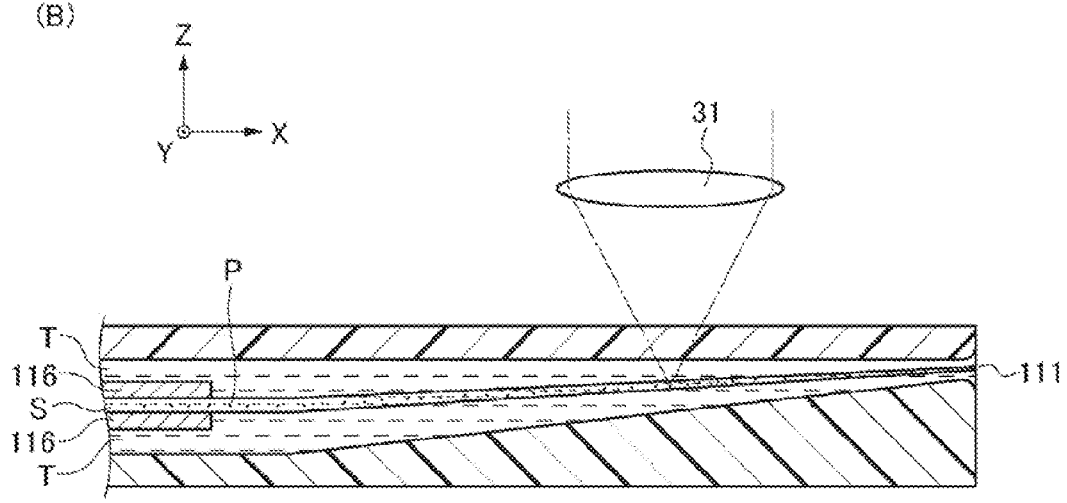

Here, the case where the laminar flow width of the 3D laminar flow formed by the minute pipe 116 is first made a width suited for detecting minute particles in the detection portion F by the narrowing portion 117 and is then made a width with which high-frequency droplets can be formed by the pressor portion 118 has been described. The narrowing of the laminar flow width in the flow path 11 does not need to be carried out in two steps of the narrowing portion 117 and the pressor portion 118 and can be carried out such that the flow path width and depth gradually and consecutively decrease from the opening position of the minute pipe 116 of the flow path 11 to the orifice 111 as shown in FIG. 14, for example.

In addition, the flow path 11 may take various shapes as long as the flow path width and depth at the opening position of the minute pipe 116, the detection portion F, and the orifice 111 part are within a range of the favorable numerical values.

Further, the shape of the opening of the orifice 111 may be an arbitrary shape such as a square, a rectangle, and a circle. Furthermore, as shown in FIG. 14, an end surface part of the opening portion may be formed in an inverse tapered shape. With such a trumpet shape of the end surface part of the opening of the orifice 111, drain of the formed droplets can be improved.

(4-3) Dispense by Charge Means

In the microchip 1, the minute pipe 116 is formed of metal to which a voltage can be applied and structured as a charge means for imparting a positive or negative charge to the sheath fluid and sample fluid flowing through the flow path 11. By applying a voltage to the sheath fluid and sample fluid by applying a voltage to the minute pipe 116 when discharging droplets of the sample fluid and sheath fluid flowing through the flow path 11 from the orifice 111, a positive or negative charge can be imparted to the discharged droplets.

By imparting a positive or negative charge to the droplets A discharged from the orifice 111 by the minute pipe 116, a positive or negative charge can be imparted to the droplets G obtained after the collision with the droplets B and C. Accordingly, the movement direction of the droplet G can be controlled by the electric repulsion force or absorption force that acts between the first paired electrodes 51, 51 and the second paired electrodes 52, 52 (see FIG. 8).

The flying direction of the droplet G after passing the second paired electrodes 52, 52 can be controlled arbitrarily in the X- and Y-axis directions in the figures by varying the voltage applied to the first paired electrodes 51, 51 and the second paired electrodes 52, 52 and adjusting the intensity of the electric action force between the droplet G. Accordingly, the droplet G can be guided to each of the plurality of areas 21 formed in the vessel 2 and retrieved in the areas. It should be noted that the control of the flying direction of the droplet G can be adjusted by varying a voltage applied to the minute pipe 116.

(4-4) Dispense by Drive Means

Figure 15:
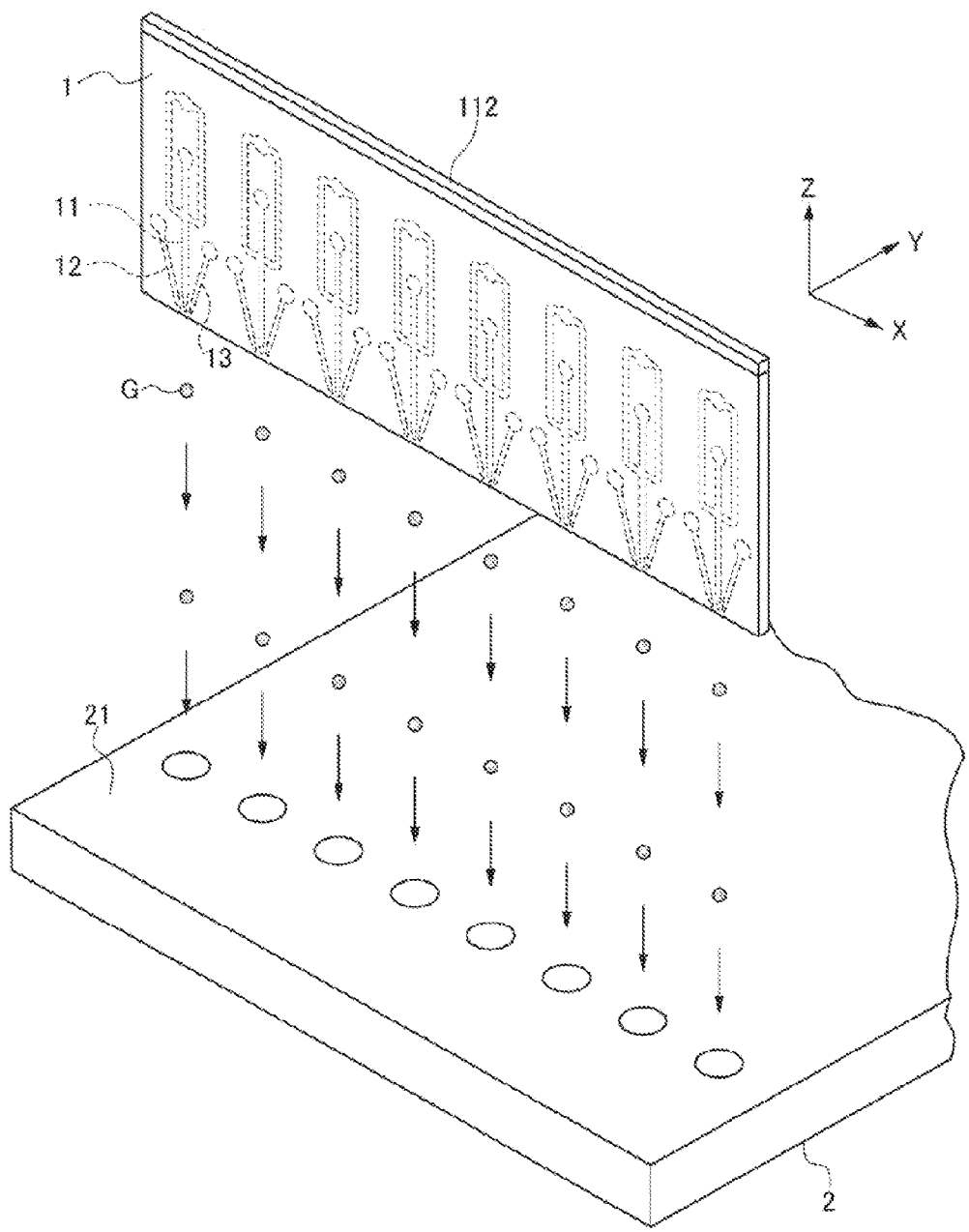
FIG. 15 A diagram for explaining a structure for dispensing mixed droplets in a microchip-type substance mixing apparatus.

FIG. 15 is a schematic diagram for explaining another structure for dispensing the droplet G obtained after the collision and mixing in the microchip-type substance mixing apparatus. The figure shows a structure for dispensing the droplet G to the plurality of areas 21 of the vessel 2 while moving the microchip 1 by a drive means.

Here, descriptions will be given on an example where the droplet G is dispensed using the microchip 1 on which a plurality of structural units constituted of the flow paths 11, 12, and 13 etc. for forming the droplet G are provided with respect to 96 wells (areas 21) formed in a multi-plate (vessel 2) (hereinafter, simply referred to as "structural unit").

In the vessel 2, 8 areas 21 are arranged in the X-axis direction, and 12 areas 21 are arranged in the Y-axis direction in the figure. Accordingly, also on the microchip 1 shown in the figure, 8 structural units are arranged in one row in the X-axis direction. The arrangement interval of the structural units coincides with the interval of the areas 21 in the X-axis direction. As a result, the mixed droplets G discharged from the structural units are retrieved in the areas 21 arranged in a row.

The microchip 1 is movable by a drive means (not shown). By sequentially moving the relative position of the microchip 1 with respect to the vessel 2 by the drive means, 0 or 1 or more droplet G can be retrieved in each of the plurality of areas 21 formed in the vessel 2. Specifically, while sequentially moving the microchip 1 in the Y-axis direction, the droplets G are dispensed to 8 areas 21 arranged in the X-axis direction every time. As described above, by forming the plurality of structural units on the microchip 1 and dispensing the mixed droplets thereto, mixing of a large number of reaction systems can be carried out in a short time.

INDUSTRIAL APPLICABILITY

In the substance mixing apparatus according to the present invention, by discharging fluids including substances to be mixed as droplets from the orifices of the flow paths and causing them to collide with one another, the substances included in the fluids can be mixed uniformly in a short time. Moreover, since the substances can be incorporated into the droplets in certain amounts, variances in the amount of substances to be mixed are not caused. Therefore, the substance mixing apparatus according to the present invention is useful for carrying out a high-speed and large-scale reaction of various compounds and may be used for various reactions and analyses such as a polymerase chain reaction (PCR) and a mass analysis.

Furthermore, in the substance mixing apparatus according to the present invention, the fluid including minute particles is discharged as droplets from the orifice of the flow path, the fluid including a substance to be mixed is discharged as droplets from the orifice of the other flow path, and the droplets are caused to collide with one another. As a result, the minute particles and substance included in the droplets can be mixed uniformly in a short time. Therefore, it is particularly useful for mixing minute particles including biologically-relevant minute particles such as a cell, a microorganism, and a liposome and synthetic particles such as latex particles, gel particles, and industrial particles with various compounds, and carrying out a high-speed and large-scale analysis on a reaction of the minute particles and compounds.

DESCRIPTION OF SYMBOLS

A, B, C, G, H droplet
F detection portion
P minute particle
S sample fluid laminar flow
T sheath fluid laminar flow
1 microchip
11, 12, 13 flow path
111, 121, 131 orifice
112, 122, 132 oscillation device
113, 123 charge means
114 sheath fluid inlet
115 sample fluid inlet
116 minute pipe
117 narrowing portion
118, 128, 138 pressor portion
124, 134 inlet
51, 52 paired electrode
2 vessel
21 area
31, 32, 33 detection means
4 control means It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. A substance mixing apparatus, comprising:
    two or more flow paths in each of which an orifice, from which a fluid that flows therethrough is externally discharged, is formed, wherein in at least one of the flow paths, the fluid includes a first fluid and a second fluid;
    a minute pipe that introduces a laminar flow of the second fluid including minute particles in a laminar flow of the first fluid in the at least one of the flow paths;
    a narrowing portion of the at least one of the flow paths, the narrowing portion being downstream from the minute pipe and having a cross sectional area that gradually narrows from an upstream side of the narrowing portion to a downstream side of the narrowing portion;
    an oscillation device that forms droplets of the fluid discharged from each of the orifices by oscillating at least the orifice part of the flow paths at a predetermined oscillation frequency and discharges the droplets such that the droplets collide with one another; and
    a detection means arranged to detect the minute particles in a detection portion of the at least one of the flow paths positioned downstream of the minute pipe and upstream of the orifice, wherein the detection portion is arranged within the narrowing portion such that a cross-sectional area of the orifice is smaller than a cross-sectional area of the detection portion, which is smaller than a cross-sectional area of the at least one of the flow paths at the upstream side of the narrowing portion.

2. The substance mixing apparatus according to claim 1, further comprising:
    a control means for calculating a flow sending interval of the minute particles based on a detection signal of the minute particles from the detection means and controlling the oscillation frequency of the oscillation device based on the calculated flow sending interval.

3. The substance mixing apparatus according to claim 2, wherein the control means controls the oscillation frequency such that a predetermined number of minute particles are incorporated in the droplets discharged from the orifices of the flow paths through which the fluid including the minute particles flows.

4. The substance mixing apparatus according to claim 3, further comprising:
    a charge means for imparting a charge to the droplets discharged from the orifices; and
    paired electrodes provided oppositely along a movement direction of the droplet obtained by the collision.

5. The substance mixing apparatus according to claim 4, wherein the movement direction of the droplet obtained by the collision is controlled by an electric action force generated by the charge imparted to the droplets discharged from the orifices and the paired electrodes.

6. The substance mixing apparatus according to claim 3, wherein the orifices of the flow paths are relatively moved with respect to two or more areas for retrieving and accommodating the droplet obtained by the collision.

7. The substance mixing apparatus according to claim 1, wherein the flow paths are formed on a single microchip.

8. A microchip used in the substance mixing apparatus according to claim 7, wherein the microchip includes the two or more flow paths.

9. The microchip according to claim 8, wherein the minute pipe is formed of metal to which a voltage can be applied.

10. The microchip according to claim 8, further comprising:
an oscillation device that oscillates at least the orifice part of the flow paths.

11. A substance mixing method, comprising:
arranging two or more flow paths in each of which an orifice, from which a fluid that flows therethrough is externally discharged, is formed, wherein in at least one of the flow paths, the fluid includes a first fluid and a second fluid, a minute pipe that introduces a laminar flow of the second fluid including minute particles in a laminar flow of the first fluid in the at least one of the flow paths, and a narrowing portion of the at least one of the flow paths, the narrowing portion being downstream from the minute pipe and having a cross sectional area that gradually narrows from an upstream side of the narrowing portion to a downstream side of the narrowing portion;
forming droplets of the fluid discharged from the orifices by oscillating at least the orifice part of the flow paths at a predetermined oscillation frequency and discharging the droplets;
causing the droplets discharged from the orifices of the flow paths to collide with one another; and
detecting the minute particles in a detection portion that is within the narrowing portion and downstream of the minute pipe and upstream of the orifice, wherein a cross-sectional area of the orifice of the flow paths is smaller than a cross-sectional area of the detection portion, which is smaller than a cross-sectional area of the at least one of the flow paths at the upstream side of the narrowing portion.

12. The substance mixing method according to claim 11, wherein droplets that include the minute particles and are discharged from the orifice of the flow path is caused to collide with the droplets discharged from the orifice of the other flow path, to thus mix the minute particles with a substance.

13. The substance mixing method according to claim 12, wherein the oscillation frequency is controlled based on a flow sending interval of the minute particles included in the fluid that flows through the flow paths, and a predetermined number of minute particles are incorporated in the droplets discharged from the orifices of the flow paths.

14. The substance mixing method according to claim 13, further comprising:
imparting a charge to the droplets discharged from the orifices;
controlling a movement direction of the droplet obtained by the collision by an electric action force generated by paired electrodes provided oppositely along the movement direction of the droplet obtained by the collision and the charge imparted to the droplets; and
dispensing the droplet obtained by the collision to two or more areas.

15. The substance mixing method according to claim 13, further comprising:
dispensing the droplet obtained by the collision to two or more areas by relatively moving the orifices of the flow paths with respect to the areas.

16. The substance mixing method according to claim 11, wherein the flow paths are formed on a single microchip.

* * * * *